(12) United States Patent
Shah

(10) Patent No.: US 10,839,020 B2
(45) Date of Patent: Nov. 17, 2020

(54) MULTI-SOURCE USER GENERATED ELECTRONIC DATA INTEGRATION IN A BLOCKCHAIN-BASED TRANSACTIONAL SYSTEM

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 358 days.

(21) Appl. No.: 16/048,338

(22) Filed: Jul. 29, 2018

(65) Prior Publication Data

US 2018/0336286 A1 Nov. 22, 2018

Related U.S. Application Data

(63) Continuation-in-part of application No. 14/686,684, filed on Apr. 14, 2015, now abandoned.
(Continued)

(51) Int. Cl.
*G16H 10/60* (2018.01)
*G06F 16/9038* (2019.01)
*H04L 9/06* (2006.01)
*G06F 1/16* (2006.01)
*G06F 16/182* (2019.01)
(Continued)

(52) U.S. Cl.
CPC ......... *G06F 16/9038* (2019.01); *G06F 1/163* (2013.01); *G06F 16/182* (2019.01); *G06F 16/907* (2019.01); *G06F 16/90332* (2019.01);
*G06Q 10/10* (2013.01); *G06Q 30/018* (2013.01); *G16H 10/60* (2018.01); *H04L 9/0637* (2013.01); *H04L 9/0643* (2013.01);
(Continued)

(58) Field of Classification Search
CPC ........ G06F 21/50; G06F 19/327; G06F 19/19; G06F 19/322; G06F 17/30864; G06Q 30/024; G06Q 50/24; A61B 5/0002; G16H 10/60
See application file for complete search history.

(56) References Cited

U.S. PATENT DOCUMENTS 5,924,074 A 7/1999 Evans
7,467,409 B2 * 12/2008 Reasor .................... G06F 21/50
726/22
(Continued)

*Primary Examiner* — John A Pauls
(74) *Attorney, Agent, or Firm* — Rahman LLC

(57) ABSTRACT

A system is provided for aggregating user generated electronic data associated with a user from a plurality of computing machines located separately without user intervention. Metadata associated with the user generated electronic data is stored in an electronic record repository database to perform natural language processing and metadata analysis of the user generated electronic data to identify user verified data and user unverified data. A data object including query statements and approval options is generated and presented on a remotely located display unit accessible by the user. An input against each of the plurality of query statements is received. The system updates the unverified data based on the received input. The user generated electronic data is then pushed into the electronic transactional system which may communicate electronic data messages among a plurality of computer stations.

20 Claims, 11 Drawing Sheets

Related U.S. Application Data

(60) Provisional application No. 61/979,020, filed on Apr. 14, 2014.

(51) Int. Cl.
  *G06F 16/907* (2019.01)
  *G06F 16/9032* (2019.01)
  *G06Q 10/10* (2012.01)
  *H04L 9/32* (2006.01)
  *G06Q 30/00* (2012.01)

(52) U.S. Cl.
  CPC ........ *H04L 9/3239* (2013.01); *H04L 2209/38* (2013.01); *H04L 2209/805* (2013.01)

(56) References Cited

U.S. PATENT DOCUMENTS

| | | |
|---|---|---|
| 8,428,968 B2 | 4/2013 | Bellam et al. |
| 8,521,565 B2 | 8/2013 | Faulkner et al. |
| 2003/0037054 A1* | 2/2003 | Dutta ............... G06F 21/6245 |
| 2003/0115591 A1* | 6/2003 | Weissmueller, Jr. .................... G06Q 30/0242 725/22 |
| 2004/0088374 A1 | 5/2004 | Webb et al. |
| 2004/0122846 A1* | 6/2004 | Chess ............... G06F 16/951 |
| 2006/0116904 A1 | 6/2006 | Brem |
| 2008/0009723 A1 | 1/2008 | Schefelker et al. |
| 2008/0055074 A1* | 3/2008 | Gao .................... A61B 5/024 340/539.13 |
| 2012/0245958 A1* | 9/2012 | Lawrence ............ G06Q 50/24 705/3 |
| 2012/0323606 A1 | 12/2012 | Ananthasubramaniam et al. |
| 2014/0278545 A1 | 9/2014 | Andrews et al. |
| 2014/0297331 A1* | 10/2014 | Vazquez ............... G16H 10/60 705/3 |
| 2015/0332283 A1 | 11/2015 | Witchey |

\* cited by examiner

MULTI-SOURCE USER GENERATED ELECTRONIC DATA INTEGRATION IN A BLOCKCHAIN-BASED TRANSACTIONAL SYSTEM

CROSS-REFERENCE TO RELATED APPLICATIONS

This application is a continuation-in-part of U.S. Ser. No. 14/686,684 filed Apr. 14, 2015 and entitled "Multi-Source Patient Generated Healthcare Data Integration in a Transactional System", which claims the benefit of U.S. Provisional Application No. 61/979,020, filed on Apr. 14, 2014 and entitled "Multi-Source Patient Generated Data Collection System and Method," the complete disclosures of which, in their entireties, are hereby incorporated by reference.

BACKGROUND

Technical Field

The embodiments herein generally relate to electronic data ingestion and management, and more particularly relate to collection of 'user generated electronic data' (UGED) that is not entered directly by the user and integration of the UGED within an electronic transactional system.

Description of the Related Art

UGED or sometimes also referred to as 'consumer generated electronic data' (CGED) encompasses forms of data that users generate or provide before it is submitted for entry into an electronic transactional system. In some cases, the UGED may be provided to the electronic transactional system on behalf of a third-party that may be a service provider, a person associated with the user, or any other individual or firm. In some cases, the UGED may be directly entered by or sourced from a user. UGED may, for example, include user's historical data reports or records, electronic diagnosis reports, biometric data, data gathered by various devices associated with the user, etc. UGED may be huge in quantity and heterogeneous in nature and difficult to be managed into the workflow of the electronic transactional system. Further, the UGED may be collected from a plurality of diverse and heterogeneous sources. Generally, in an environment, decisions may be made based on the UGED supplied by the users themselves or through other parties and accumulated in the electronic transactional system. Decision makers such as various professionals or practitioners may not be sure of completeness, accuracy, trustworthiness, and reliability of this data. Either the professionals completely rely on it or completely disregard it due to concerns of reliability and validity based on the degree of complications associated with such a decision making by a practitioner. It is not known who is responsible for completeness or accuracy of such UGED if the UGED is not directly entered by the user.

Further, incorporation of biometric or devices-related data into the electronic transactional system makes the decision making and workflow even more complex. The intensity of complexity may increase as there is an increase in the level of control of the devices by a user. For example, data from a plurality of user-associated devices such as for exercise management, diet management, weight management, etc. may make integration of the UGED even more confusing and complex due to increased lack of reliability, trust, validity, and no clarity about the authority for responsibility of data completeness and accuracy in the electronic transactional system. There is always a possibility that fake data may be entered by someone on behalf of a user. The fake data may arrive from institutions or persons other than the user. There have been cases where malware is uploaded through mobile communication devices or smart phones, etc. that access user records repositories and submit fake data which corrupts the records in the electronic transactional system leading to wrong decision making. Such and other issues may arise if the UGED is not entered by the user himself and the UGED is gathered without user awareness or with no control of user over data flow even if the user is aware of the data flow in the electronic transactional system.

Existing methods and systems provide a controlled access by users to electronic transactional systems and allow entry of data by the users themselves. U.S. Pat. No. 8,428,968 for example provides such a system and method wherein patients are allowed to enter data in an EMR themselves. The system, based on certain predefined physiology values, determines accuracy and validity of the patient-entered data. If the patient-entered data does not fit within the defined values, the patient is requested to confirm the patient-entered data. U.S. Pat. No. 8,428,968 focuses on data that is directly entered by the patient but does not teach solutions to reliability issues that arise when the data is not entered by the patient himself. U.S. Pat. No. 8,428,968 does not provide a system or method to allow ensuring data completeness and reliability of the patient generated data that is not directly entered or sourced from the user.

In light of the above, there is a need for an improved system and method for ensuring reliability, trust, accuracy, and completeness of the UGED for integration in an electronic transactional system, wherein the UGED is derived from a variety of associated devices and user data sources but not directly entered or sourced from the user thereby causing a major concern for accuracy, reliability and completeness during integration with the electronic transactional system.

SUMMARY

In view of the foregoing, an embodiment herein provides a blockchain-enabled system that includes a plurality of wearable devices and a cloud gateway agent server. The cloud gateway agent server receives and aggregates user generated electronic data associated with a user and acquired without user intervention from one of the plurality of wearable devices located separately, wherein the user generated electronic data comprises a plurality of computer executable data files residing in the plurality of wearable devices. The system further includes an electronic record repository database communicatively coupled with the cloud gateway agent server and stores the plurality of computer executable data files and metadata associated with the plurality of computer executable data files. The system includes a processing circuit that performs natural language processing and metadata analysis of the plurality of computer executable data files to identify user verified computer executable data files and user unverified computer executable data files from among the plurality of computer executable data files. The processing circuit further generates a computer data object including a plurality of query statements and approval options corresponding to each of the unverified computer executable data files. The processing circuit transmits the computer data object to an external computing machine at the user along with the unverified computer executable data files outputted on a remotely located display unit connected operatively with the external computing machine through an automatically generated notification by the processing circuit, wherein the computer data object represents an integrated view of the user generated electronic data residing on the plurality of wearable devices. The processing circuit updates the unverified computer executable data files as new verified computer executable data files in the electronic record repository database based on an input received from the external computing machine signifying verification of the unverified computer executable data files by the user.

The system further includes a rules engine communicatively coupled with the processing circuit and that executes a set of programmable rules including dictionary references, and user verification references to govern user approval, the metadata analysis and the natural language processing, wherein the rules engine determines the verification of the user verified computer executable data files by applying rules regarding user approval for different types of electronic data.

The system includes a blockchain-based identity authorization device connected communicatively to the rules engine to verify identity of the user in association with the set of programmable rules before granting access rights to the user for verification of the unverified computer executable data files, wherein the blockchain-based device comprises one or more of an audio recognition device, an image recognition device, and sensor modalities including a global positioning system. The system includes an electronic transactional system communicatively coupled with the electronic record repository database and the processing circuit through the cloud gateway agent server and retrieves and stores the user verified computer executable data files and the new verified computer executable data files from the electronic records repository database, and communicates electronic data messages among a plurality of computer stations located at users, service providers, and third entities, wherein the electronic data messages are obtained from the user verified computer executable data files and the new verified computer executable data files. The electronic transactional system further includes a social networking application that dynamically changes social networking connections by interacting with the electronic transactional system and by accessing the verified computer executable data files.

The system includes a communications transmitter coupled with the electronic transactional system that transmits the electronic data messages to the plurality of computer stations identified by a user approval. The computer data object includes embedded digital text-based information of the user generated electronic data that is displayed on the display unit by launching a gateway software application. The processing circuit homogenizes the user generated electronic data in a defined standard compliant format by executing computer executable data files containing the user generated electronic data. The processing circuit automatically associates a numerical trust score with each of the new verified computer executable data files by using the user input signifying the verification. The processing circuit determines verification patterns by using a machine learning algorithm, and automatically classifies the computer executable data files into the user unverified computer executable data files and the user verified computer executable data files by using the verification patterns.

In an embodiment, at least a portion of the user generated electronic data contained in at least one of the plurality of computer executable data files may be obtained by the cloud gateway agent server from a computing machine other than at the user. The at least a portion of the user generated electronic data may be obtained from the computing machine at a service provider of the user. In an embodiment, each of the plurality of wearable devices may be operatively coupled with an extensible agent appliance that launches a gateway application configured to pair the plurality of wearable devices with the cloud agent server to allow access of the plurality of computer executable data files residing on the plurality of wearable devices by the cloud agent server. The cloud agent server may install the gateway application remotely on the plurality of wearable devices through the extensible agent appliance. The gateway application may be launched at the external computing machine associated with the user to allow the user to view sources of the unverified computer executable data files and to verify the unverified computer executable data files through a single-clickable user executable response against one of the approval options.

The electronic transactional system may include a filter circuit such that the filter circuit rejects the plurality of computer executable data files from being pushed into the electronic transactional system if the trust score associated with the plurality of computer executable data files is below a threshold limit. The processing circuit may perform natural language processing on an embedded user natural language text note contained digitally in the plurality of computer executable data files.

An embodiment herein provides a blockchain-enabled system that includes a plurality of devices including at least one wearable device associated with a user. The system includes a cloud gateway agent server that receives and aggregates user generated electronic data associated with the user and acquired without user intervention from one of the plurality of devices located separately, wherein the user generated electronic data includes a plurality of computer executable data files residing in the plurality of devices. The system includes a blockchain database communicatively coupled with the cloud gateway agent server and stores the plurality of computer executable data files and metadata associated with the plurality of computer executable data files.

The system includes a processing circuit that identifies user verified computer executable data files and user unverified computer executable data files from among the plurality of computer executable data files and generates a computer data object including a plurality of query statements and approval options corresponding to each of the unverified computer executable data files. The processing circuit transmits the computer data object to an external computing device at the user along with the unverified computer executable data files outputted on a remotely located display unit connected operatively with the external computing device through an automatically generated notification by the processing circuit, wherein the computer data object represents an integrated view of the user generated electronic data residing on the plurality of devices associated with the user. The processing circuit updates the unverified computer executable data files as new verified computer executable data files in the blockchain database based on an input received from the external computing device signifying verification of the unverified computer executable data files by the user.

The system further includes a blockchain-based identity authorization device to verify identity of the user before granting access rights to the user for verification of the unverified computer executable data files, wherein the blockchain-based device includes one or more of an audio recognition device that generates identity information in the form of a digital audio signal for voice recognition based on pre-stored voice patterns, an image recognition device that includes an image acquisition device to receive signals containing image patterns and facial expressions for verifying identity based on image patterns, and a global positioning system-based device that receives signals containing location details for verifying identity of the user based on its location.

The system further includes an electronic transactional system communicatively coupled with the blockchain database and the processing circuit through the cloud gateway agent server. The electronic transactional system retrieves and stores the user verified computer executable data files and the new verified computer executable data files from the blockchain database and communicates electronic data messages to a plurality of computer stations located at different locations. The electronic data messages are obtained from the user verified computer executable data files and the new verified computer executable data files. The system further includes a communications transmitter coupled with the electronic transactional system that transmits the electronic data messages to the plurality of computer stations identified by a user approval.

The audio recognition device may include a sound card adapted to receive identity information of the user in the form of a digital audio signal. The image acquisition device of the image recognition device may include a camera for taking still or streaming images. The image recognition device may include a plurality of multichannel amplifiers such that each amplifier of the multichannel amplifiers is defined to receive a specific type of sensed information from the camera sourcing signals for the image recognition device. The image recognition device may include a microcontroller, wherein the image acquisition device may be adapted to receive a digital signal and transmit the digital audio signal to the microcontroller for image recognition based on pre-stored image patterns.

In an embodiment, at least a portion of the user generated electronic data contained in at least one of the plurality of computer executable data files may be obtained by the cloud gateway agent server from a computing machine other than at the user. In an embodiment, each of the plurality of devices may be operatively coupled with an extensible agent appliance that launches a gateway application configured to pair the plurality of devices with the cloud agent server to allow access of the plurality of computer executable data files residing on the plurality of devices by the cloud agent server. The cloud agent server may install the gateway application remotely on the plurality of devices through the extensible agent appliance.

The system may further include a blockchain device that may include a specific blockchain-enabled server device and a smart device running a custom dedicated software application, wherein the smart device is configured to engage in communication with the blockchain-enabled server device. The blockchain device may generate a smart contract configured to automatically validate a transaction using a special key over a plurality of computer executable distributed blockchain ledgers such that each of the plurality of computer executable distributed blockchain ledgers may contain a copy of the computer executable data files. The blockchain device may further include a distributed trusted ledgers system that may store the distributed blockchain ledgers over a blockchain integrity network for secured and controlled access by the user through a private key.

The processing circuit may prevent voice inputs from being received by the audio recognition device upon a predetermined number of unsuccessful voice inputs being entered into the audio recognition device and not authorized or identified by the processing circuit. The processing circuit may prevent visual inputs from being received by the image recognition device upon a predetermined number of unsuccessful visual inputs being entered into the image recognition device and not authorized or identified by the processing circuit. The processing circuit may transmit a user-access denial output signal upon not authenticating an identify of a user.

BRIEF DESCRIPTION OF THE DRAWINGS

The features of the disclosed embodiments may become apparent from the following detailed description taken in conjunction with the accompanying drawings showing illustrative embodiments herein, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In the following detailed description, reference is made to the accompanying drawings which form a part hereof, and in which is shown by way of illustration specific embodiments in which the embodiments herein may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

Figure 1:
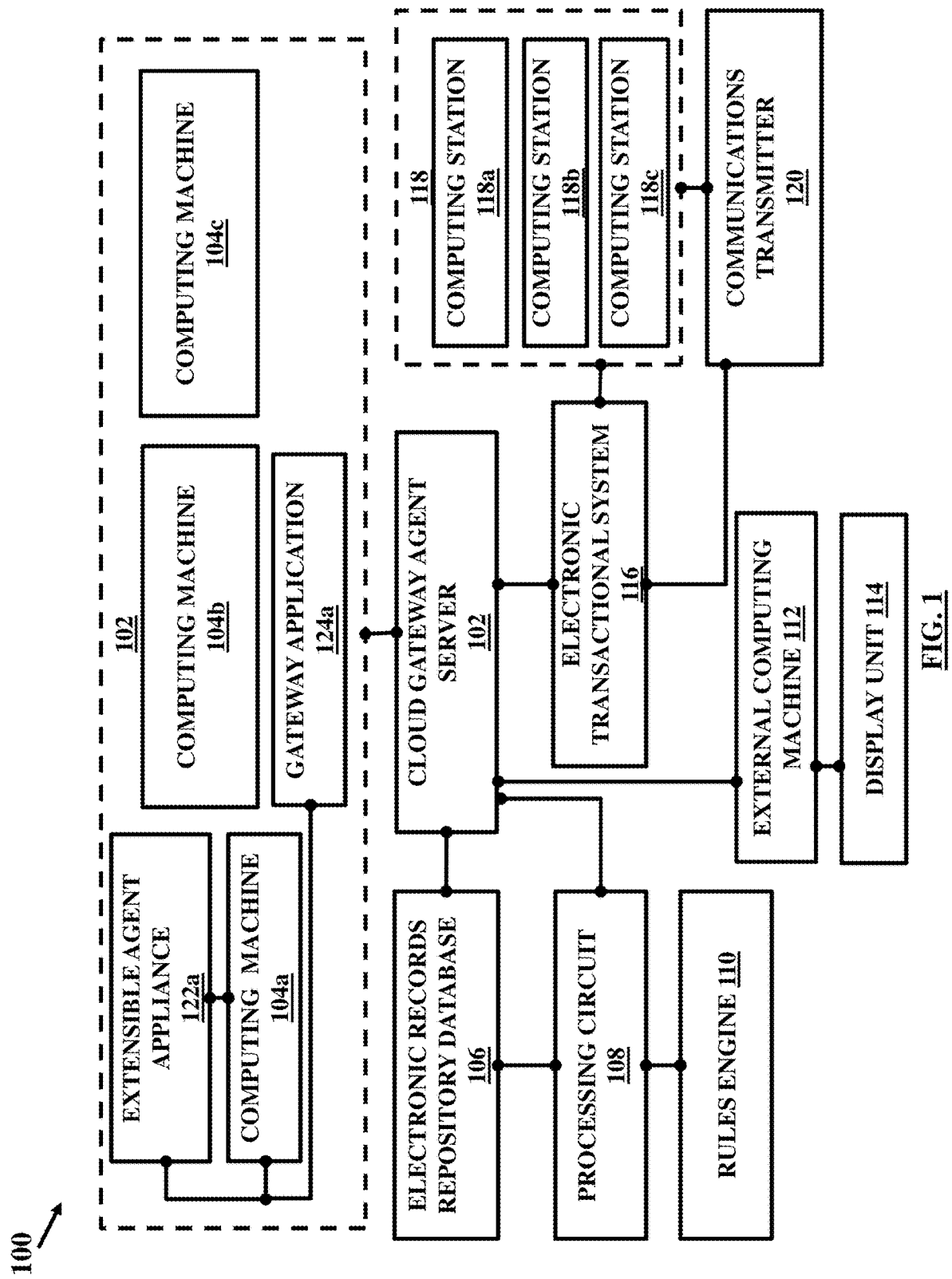
FIG. 1 illustrates an ecosystem including an electronic transactional system for integration of user generated electronic data (UGED) in accordance with an embodiment herein.
Figure 10:
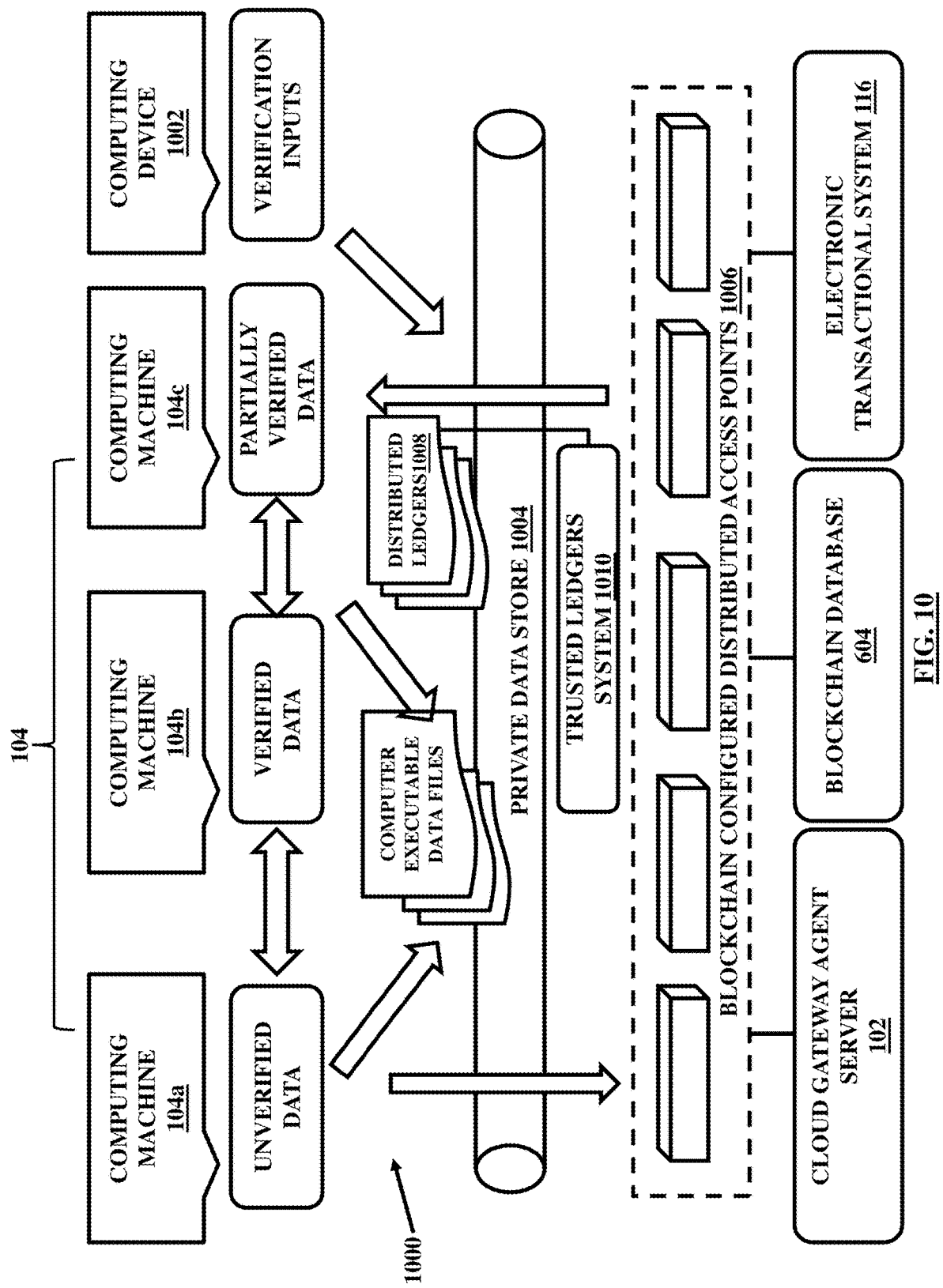
FIG. 10 illustrates an architecture for enabling an authentication, an access, and a verification mechanism to access and verify digital records (UGED), in accordance with the embodiments herein.

FIG. 1 illustrates an overview of ecosystem 100 for integration of User Generated Electronic Data (UGED) in an electronic transactional system. The ecosystem 100 includes a cloud gateway agent server 102 to receive and aggregate the UGED associated with a user from a variety of sources. The UGED may reside on a plurality of computing machines 104a, 104b, and 104c together referred to as 104 (as indicated in FIG. 10) located separately and remote from one another and remote from the cloud gateway agent server 102. The UGED resides on the plurality of computing machines 104a-104c in the form of a plurality of computer executable electronic data files. For example, the UGED in the computer executable electronic data files can include two-dimensional images, three-dimensional images, digital and/or analog images, and/or digital and/or analog video of a user's internal organ or surrounding features. Also, text files can be generated, including notes, comments, prescription notes, and/or user history.

A variety of data sources that may be coupled to the plurality of computing machines 104a-104c or be included in the plurality of computing machines 104a-104c or may serve as the plurality of computing machines 104a-104c may include such as electronic data systems, material management systems, clinical trial systems, consumer and user electronic systems, managed care systems, telemedicine systems, service provider data systems, core transaction systems, clinical data repositories, workflow systems, behavior data systems, decision support systems, user relationship management systems, workforce enabling systems, imaging systems, electronic data capture systems, electronic data management systems, integrated devices, labs systems, clinical trials systems, user family and community engagement systems, social user relationship management systems, user consent, permissions and disclosure management systems, user communications systems, social networking platforms or social networking engines, and the like without limitations.

In accordance with some embodiments herein, the UGED is aggregated without any user intervention. In accordance with some embodiments, the UGED is aggregated from the plurality of computing machines 104a-104c with limited user intervention. In an example, the plurality of computing machines 104a-104c may be located remotely from the user and the UGED is aggregated from the plurality of computing machines 104a-104c without any user intervention such that the user is not aware about or involved during receipt or access of the UGED from the plurality of computing machines 104a-104c or during generation of the UGED from the user by a computing machine such as the computing machine 104a or a service provider associated with the computing machine 104a. The plurality of computing machines 104a-104c in such a case may be located at service provider end in an example. For example, the user may have submitted his electronic data in various data sources at the service provider or devices associated with the user may have generated data which may be gathered and stored in a storage device at the service provider without any user intervention or control over data acquisition or without any awareness by the user of data access and collection by the service provider or without any control of review or verification of the UGED by the user even if he is aware of data generation and collection by the computing machine 104a. In accordance with some embodiments, the UGED may refer to electronic data generated from various user-associated devices or collected by the service provider and stored with the service provider without user control or intervention. The UGED as defined herein is not directly entered by the user for submission with the cloud agent gateway server. The UGED can be submitted by the user to the computing machine 104a or the service provider without any control over review and verification or confirmation of the UGED. In accordance with some embodiments herein, the UGED refers to data acquired from various sources coupled to or included within the plurality of computing machines 104a-104c without any user intervention in accordance with various data aggregating scenarios discussed hereafter without limitations.

In accordance with an embodiment herein, the computing machine 104a may be situated at a multiple service provider setting in an acute care environment such that the user whose UGED is acquired through the computing machine 104a is unconscious. The user is not in a state and has no capability of verifying the UGED and any generation or acquisition of the UGED may be considered without user intervention. In an example, the computing machine 104a may be a device associated with the user that generates or collects the UGED (without any knowledge of the user) for being acquired by the cloud gateway agent server 102. However, the user is aware of the fact that he was present in the service provider setting and therefore can review, verify, and/or authorize the UGED later upon receipt of a request from the cloud gateway agent server 102.

In accordance with an embodiment, the computing machine 104a may be situated at a service provider setting such that the user is not unconscious but the care is provided by a service provider. The user does not have any choice or control over the UGED being generated by the computing machine 104a situated at the service provider or the service provider setting. The user can see the UGED being generated by the computing machine 104a such as a device etc. but the user is incapable to monitor or review the UGED being generated or captured. The user is though aware of the data being generated and acquired to be pushed into the electronic transactional system but has no control or choice over review and verification. In this scenario, the user is not unconscious but still does not have any control to intervene and the UGED so generated and acquired by the cloud gateway agent server 102 may be considered to be acquired without user intervention.

In accordance with an embodiment, the service provider may visit the user and collect the UGED thorough the computing machine 104a which can then transmit the UGED to the cloud gateway agent server 102 for being pushed into an electronic transactional system such as the electronic transactional system 116 as described below. The user is, however, aware of the generation and collection of the data by the service provider or the computing machine 104a but has no control over verification of the UGED. The UGED so aggregated by the cloud gateway agent server 102 may not be verified for completeness or accuracy or ownership.

In accordance with another embodiment, the service provider may provide a device to the user that may include or be coupled to or serve as the computing machine 104a that generates and collects the UGED from the user. The user may control and use the device but may have no control over data verification and review. The data may be erroneous. The UGED so gathered by the device may be provided to the service provider for further use in the electronic transactional system 116.

In accordance with another embodiment, the UGED may be generated and collected by a wearable device that may be coupled to or may include or that may serve as the computing machine 104a and is capable of data exchange with the cloud gateway agent server 102. The wearable device generates data from the user but the user has no control with intervention over data editing, data review, data verification or authorization. The wearable device may transmit the UGED to the cloud gateway agent server 102 upon notification of request without any user intervention. The cloud gateway agent server 102 may not even know that the UGED is acquired from the wearable device unless it is verified by the user later, in an example.

In accordance with various embodiments, the user may be aware, or not, about generation and collection of the UGED by the computing machine 104a but the aggregation of the UGED by the cloud gateway agent server 102 and/or the generation or collection of the UGED by the computing machine 104a occurs without any user intervention such that the user has no control to verify, review and/or authorize the UGED for sharing with other people. In some embodiments, even if the user has some limited control of intervention and a portion of the aggregated UGED is verified by the user, entire UGED associated with the user may not be verified and/or reviewed by the user. Hence, reliability of the entire UGED is not high enough to trust unless it is verified by the user in its entirety. There is always a possibility that some portion of the UGED may be unverified.

In an example, the cloud gateway agent server 102 may host a series of server components and server applications such as agent admin server and agent admin applications, gateway monitor server and gateway monitor applications, processing circuits and other hardware and software components or modules or applications that act as a secure conduit between the cloud agent gateway server 102 and external cloud systems.

The ecosystem 100 further includes an electronic record repository database 106 communicatively and operatively coupled with the cloud gateway agent server 102 to store the plurality of computer executable electronic data files and metadata associated with the plurality of computer executable electronic data files. The metadata associated with the plurality of computer executable electronic data files may be indicative of details about the user, such as name, age, gender, user verification status, and the like.

The electronic record repository database may include a row store, a column store, a file store, a graph store, and various other stores for storing the UGED contained in the plurality of computer executable electronic data files. The UGED may include structured data, coded data, semi-structured data, unstructured data, scanned data, and the like. The electronic record repository database 106 may include a database management system such as a relational database management system or of other type to handle large amounts of data obtained from the plurality of computing machines 104a-104c. In an example, the computer executable electronic data files (or computer executable data files) stream through the cloud gateway agent server 102 as and when such files are received from the plurality of computing machines 104a-104c. In another example, the computer executable data files may be received on-demand by the cloud gateway agent server 102 from the plurality of computing machines 104a-104c and accordingly pushed into the electronic records repository database 106. In accordance with this example, a data flow management circuit may be coupled with the electronic records repository database 106 and the cloud gateway agent server 102 to control flow of the computer executable data files from the plurality of computing machines 104a-104c on-demand by the cloud gateway agent server 102.

The ecosystem 100 further includes a processing circuit or a processor 108 coupled communicatively and operatively with the cloud gateway agent server 102 and the electronic records repository database 106. The processing circuit 108 is configured to perform natural language processing and metadata analysis of the plurality of computer executable data files to identify user verified computer executable data files and user unverified computer executable data files from among the plurality of computer executable data files aggregated from the plurality of computing machines 104a-104c. The processor 108 may include or be coupled communicatively and operatively with a rules engine 110. The rules engine 110 may be configured to execute a set of programmable rules including dictionary references, and user verification references to govern user approval of the computer executable data files, metadata analysis and natural language processing. The rules engine 110 may store the dictionary references for allowing the processing circuit 108 to perform semantic analysis, metadata analysis and natural language processing. The user verification references may contain rules regarding user approval for different types of electronic data which in association with a metadata analysis output and a natural language processing output of the computer executable electronic data files results in determination of and classification among the user verified computer executable data files and the user unverified computer executable electronic data files (referred to interchangeably hereafter as verified computer executable data files and unverified computer executable data files without limitations).

The embodiments herein may employ natural language processing to identify the user verified computer executable data files and the user unverified computer executable data files. The processing circuit 108 may look for specific terms to identify the verified and unverified computer executable data files or user verified and unverified UGED. The UGED, in an embodiment, may be stored as an unstructured component such as embedded in a note. The note may, for example, include physiological lab-oriented data of the user that the user could never verify. In an example, the note may read that the user's fever at a defined service provider setting measured 99° C. The note may be stored as a natural text, in an example. The processing circuit 110 may employ the natural language processing on the physiological data embedded in the note to extract the specific terms such as terms related to 'physiological' etc. and data collection terms such as 'user' from the natural text that might have been recorded by the service provider as a user record. If the note reads, for example, that the user met the service provider and verified the data collected by the service provider from the note, the processing circuit 108 may associate high reliability score to the UGED and consider it as verified UGED.

In an example, the UGED may be obtained from electronic records of the service provider such that verification status by the user may be maintained in the electronic record by the service provider. For example, the note from the service provider may read that the UGED was verified or not by the user when he was conscious after surgery or the electronic record may be silent about verification by the user so that the UGED may be classified by the processing circuit 108 as verified or unverified based on what the note says. In another embodiment, the UGED may be obtained from the electronic record of the service provider but irrespective of the verification status of the user mentioned in the note, the processing circuit 108 may look for a user-driven separate user verification status from the user. The user-driven verification may be obtained even if the service provider electronic record in the form of the note reads that the UGED is verified by the user in such cases.

In an embodiment, the processing circuit 108 may perform natural language processing to discover new verification patterns across the UGED based on old verification patterns. For example, if the processing circuit 108 finds six different user notes from different service providers in which the term 'user' is mentioned wherein the UGED contained in each of the six notes is mentioned to be verified by the user, the processing circuit 108 may utilize machine learning algorithms to determine new verification patterns based on the old verification patterns and automatically verify the UGED and increase its reliability considering that it looked similar to what the user had already verified in accordance with the old verification patterns.

The processing circuit 108 is further configured to generate a data object including a plurality of query statements and approval options corresponding to each of the unverified computer executable data files as identified from the metadata analysis, and natural language processing by the processing circuit. The query statements may define a set of questions for seeking a user approval for the unverified computer executable data files such that a response for the query statements by the user may be represented through one of the approval options thereby verifying or dispute the user generated electronic data contained in the unverified computer executable electronic data files. The data object may represent an integrated view of the user generated electronic data or the unverified computer executable data files residing on the plurality of computing machines 104a-104c. The processing circuit 108 transmits the data object to an external computing machine 112 associated with the user along with the unverified computer executable electronic data files. The data object may be outputted on a remotely located display unit 114 connected operatively with the external computing machine 112. In an example, display of the data object may be activated through an automatically generated notification by the processing circuit 108 which may be received by the external computing machine 112.

The verification of the UGED confirms belonging and ownership of the UGED contained in the computer executable data files or the unverified computer executable data files represented through the data object. The approval options may be indicative of verifying the UGED contained in the unverified computer executable data files as belonging to the user or not belonging to the user which signifies whether the UGED collected from sources other than from the user (such as service provider) truly belongs to the user and is trustworthy and reliable or does not belong to the user and is not trustworthy and reliable. This is more important to verify because the UGED is not directly entered by the user but received from sources other than the user or even if collected from devices associated with the user, the user does not have any control to review or verify the UGED. Even if the UGED is acquired from associated devices, the aggregation and retrieval of the UGED is done without any user intervention and is purely relied on the trustworthiness of the service provider from where the UGED is aggregated or relied on the accuracy and reliability of devices connections unless the UGED is verified by the user himself as is discussed herein. Based on a reply option from the user in response to each of the query statements for each of the unverified computer executable data files, a user input may be received by the cloud agent gateway server 102. The user input may signify reliability and trustworthiness of the unverified computer executable data files and the UGED contained therein.

The processing circuit 108 updates the unverified computer executable data files as new verified computer executable data files in the electronic record repository database 106 based on the input received from the external computing machine 112 signifying verification of the unverified computer executable data files by the user. The new verified computer executable data files may include data elements that may be identified as accurate and belonging to the user as indicated by the user input, or may include data elements that may be identified as inaccurate and not belonging to the user as indicated by the user input or a combination of both. Even if the data elements are not accurate or complete which may represent that all or a portion of the UGED does not belong to the user and is wrongly attributed to the user or is incomplete, the UGED or a portion thereof is still considered as verified but wrong or incomplete data. The processor or processing circuit 108 may store the unverified computer executable data files as the new verified computer executable data files in the electronic record repository database with a first indicator if the input is indicative of the user generated electronic data contained in the unverified computer executable data files to be reliable and belonging or rightly attributed to the user. The processing circuit 108 may store the unverified computer executable data files as the new verified computer executable data files in the electronic record repository database 106 with a second indicator if the input is indicative of the UGED contained in the unverified computer executable data files to be non-reliable and not belonging to the user and wrongly attributed to the user. The processing circuit 108 may also store the first indicator and the second indicator along with the new verified computer executable data files such that the first indicator and the second indicator can facilitate in categorization of verified and unverified data and reliable or non-reliable UGED in future once more user generated electronic data comes in and gets aggregated by the cloud gateway agent server 102 in the electronic record repository database 106.

In an example, the UGED residing in the form of the plurality of computer executable data files is aggregated by the cloud gateway agent server 102 from sources located at service provider end. In an example, the user generated electronic data may be aggregated from devices associated with the user such as wearable devices serving as the plurality of computing machines 104a-104c. The user generated electronic data can in such cases be obtained directly from the wearable devices or machines networked through a network with the cloud gateway agent server 102 and capable of data exchange and associated with the user in a service premise such as the hospital, nursing home, or any other service provider premise or even at a user home. Since the UGED is not directly entered by the user himself, there remains a possibility of non-reliability, inaccuracy, incompleteness of the data and therefore verification of the UGED is performed by the cloud gateway agent server 102 and associated devices as discussed above and later to verify by the user himself whether the data belongs to the user and is rightly and completely attributed to him. Further, since in a hospital or any other service provider premise, several users are admitted and there may be a possibility of errors and data exchange among different users, it becomes extremely important to verify the UGED so as to reliably use the UGED through various electronic transactional systems for data exchange for a variety of purposes. One such transactional system 116 is discussed hereafter. In accordance with an exemplary embodiment, it is to be understood that the UGED for use by the electronic transactional system 116 is obtained from the service provider directly or from the devices associated with the user at service provider so as to ensure the UGED is properly interpreted by the service provider also for technical details and verified by the service provider also and is ready for use by several other entities through the electronic transactional system 116. In accordance with an exemplary embodiment, the plurality of computing machines 104a-104c from where the UGED is aggregated reside at the service provider end and the UGED is expert driven that is verified by the service provider. In an example, the UGED is not entered by the user or sourced from the user as it may lead to inaccuracy due to weak understanding or lack of expert understanding of technical details of the UGED by the user.

Figure 3:
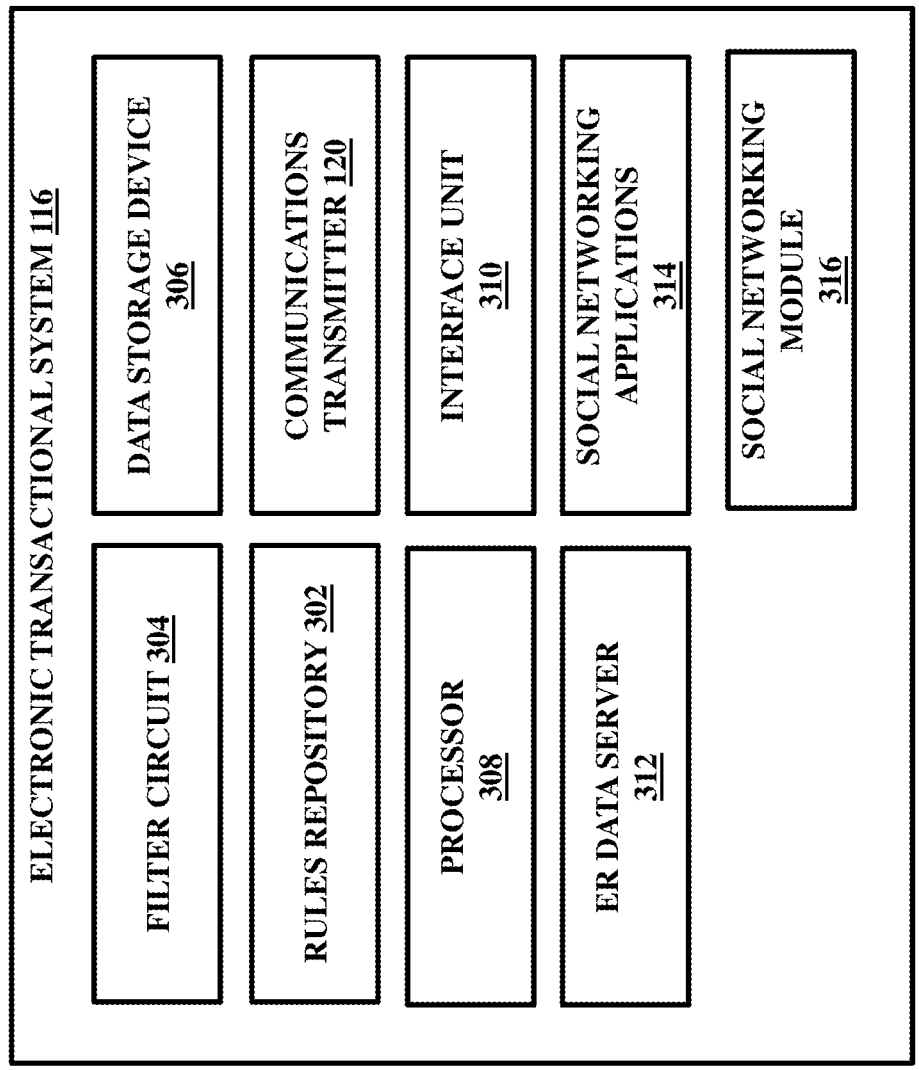
FIG. 3 illustrates an exemplary electronic transactional system, in accordance with an embodiment herein.

The ecosystem 100 may include the electronic transactional system 116 which may be communicatively coupled with the electronic record repository database 106 and the processing circuit 108 through the cloud gateway agent server 102. The electronic transactional system 116 is configured to retrieve the user verified computer executable data files and the new verified computer executable data files from the electronic records repository database 106 and store them in a separate data storage device such as the data storage device 306 as shown in FIG. 3 that may be included within the electronic transactional system 116 or may be operatively and communicatively coupled with the electronic transactional system 116. The electronic transactional system 116 may be accessible by a plurality of computing stations 118a, 118b, and 118c together referred to as 118 located at users, service providers, and other entities or entities that may access the UGED at least in part in accordance with user approval guidelines for access defined by the electronic transactional system 116. The electronic transactional system 116 may be coupled operatively with or may include a communications transmitter 120 for transmitting data messages to the plurality of computing stations 118 identified by a user approval. The data messages may include information requested by the plurality of computing stations 118 and derived from the verified computer executable data files and the new verified computer executable data files. It must be appreciated that the cloud gateway agent server 102 executes user verification of the plurality of computer executable data files by the user so as to ensure that the various entities are allowed to access verified UGED from the electronic transactional system 116. In an example, the embodiments herein therefore provide a mechanism for using by the entities reliable and trusted user-verified UGED that is already aggregated from expert driven sources such as service provider or through automated devices such as wearables etc. The UGED thus used by the entities for a variety of complex purposes is not only well interpreted by experts or service providers but also verified for completeness and user ownership by the user himself before integration with the electronic transactional system 116. This ensures that the UGED is trustworthy enough and is also interpreted correctly.

In accordance with an embodiment herein, each of the plurality of computing machines 104a-104c is coupled operatively and communicatively to an extensible agent appliance such as the computing machine 104a is coupled to an extensible agent appliance 122a. In an example, the extensible agent appliance 122a may be configured to host a plug and play cloud agent. The plug and play agent may include a central host such that various functionalities are added to it as separate plug-ins. New plug-ins as received from the cloud gateway agent server 102 may be automatically added into the plug and play agent. The plug and play agent can be installed by a user associated with the computing machine 104a or may be installed by the cloud agent gateway server 102. The extensible agent appliance 122a is capable of launching a gateway application 124a configured to pair a connected computing machine 104a with the cloud gateway agent server 102 to allow access of computer executable data files residing on the computing machine 104a by the cloud agent server 102. The gateway application 124a allows and automates transfer of the computer executable data files from the computing machine 104a to the cloud agent gateway server 102. In an example, a similar extensible agent appliance may be associated with the external computing machine 112 associated with the user for verification of the UGED. A similar gateway application may be launched at the external computing machine 112 for use by the user to receive the unverified computer executable data files from the cloud agent gateway server 102 for verification. The gateway application at the external computing machine 112 may allow the user to view the unverified computer executable data files, sources of the unverified computer executable data files and to verify the unverified computer executable data files through a single-click user executable response against one of the approval options. For example, the user may simply mark 'YES' or 'NO' as one of the two approval options against the question statements in an embodiment. In this example, 'YES' may for example indicate that the unverified computer executable data files belong to the user and 'NO' may indicate that the unverified computer executable data files do not belong to the user. Any attribution of these files marked as 'NO' to the user is to be considered wrong.

In accordance with various embodiments, the user may be provided with an option or mechanism to verify the UGED generated from the user either through the devices or wearables or by service providers and aggregated without user intervention by the cloud gateway agent server 102. The user may also be provided with an option to authorize collection of the UGED and/or authorization for others to view the UGED.

In an embodiment herein such that the computing machine 104a is or includes or is coupled to a wearable device, the user may give initial pre-authorization to collect the UGED by the wearable device. In an example, the mere use of the wearable device by the user may be considered as pre-authorization to collect the UGED by the wearable device or the associated computing machine 104a. The user may also give pre-authorization to share the UGED to others or to some specific persons or entities or institutions. The user may however not always have control over review, editing, completing or verification of the UGED. There are possibilities that the UGED so aggregated from the wearable device or the attached computing machine by the cloud gateway agent server 102 may not be reviewed or verified by the user.

In an embodiment herein such that the user is unconscious in a service setting, the user may not be capable to authorize collection of the UGED by the computing machine 104a. The user cannot even review, verify or complete the UGED. The UGED so aggregated by the cloud gateway agent server 102 and unverified by the user is not reliable.

In accordance with an embodiment where the user may be conscious and is aware of collection of the UGED by a device or a service provider but does not have control over review and verification of the UGED, the user may provide pre-authorization of collection of the UGED because the UGED is collected in front of the user. The user may also confirm sharing of the UGED to other persons. In some cases, the user may not have control over review and verification of the UGED. However, upon request from the cloud gateway agent server 102 for verification, the user may verify that the UGED is correct and rightly attributed to him or not because he was present in the service setting when the UGED was collected.

In some examples, the UGED may be collected in a digital format from the devices such that the user is admitted in an acute care setting. The user has typically no control over data review and verification in the acute care environment and the files aggregated from the computing machines without user intervention may contain data that is not verified by the user himself.

In an embodiment, a service provider may use his predefined equipment on the user so that the UGED collected by the service provider through his device is not verified by the user himself. The user only authorizes the service provider to use his equipment. The user may not intervene during supply of the UGED to the cloud gateway agent server 102 and the UGED may remain unverified which is checked by the cloud gateway agent server 102 during aggregation of the UGED as discussed earlier.

In accordance with some embodiments, though the user may have control of pre-authorization to collect data by a service provider or a device and the like and may also pre-authorize or de-assign sharing of the UGED to others, it is possible, however, that the user may not always have control to review and verify the UGED before it is aggregated to the electronic transactional system 116 or to the cloud gateway agent server 102. There remains a possibility that the UGED stored in the form of computer executable data files and aggregated by the cloud gateway agent server 102 may contain unverified data also. The unverified data may cause a wrong decision-making by others using the UGED through the electronic transactional system 116.

Further, in some embodiments, the UGED may be collected by devices of a service provider and in some other cases the UGED may be collected from the user by devices owned by the user himself. These devices may be connected to the plurality of machines 104a-104c which is networked to the cloud gateway agent server 102. There is always a high risk of the UGED not verified by the user when the devices are not owned by the user. In case the UGED collected from the user is wrong, the user or the associated external computing machine 112 may respond to the query statements through one of the reply options that the UGED is wrong. For example, the user may say that the temperature record is not 99° C. as mentioned. The user may even be allowed to correct the UGED.

The UGED that is verified by the service provider only comprises a low reliability data with a low score associated with it. If the UGED is verified by the user himself, the score rises very high and the UGED may be considered as high reliability data.

Figure 2:
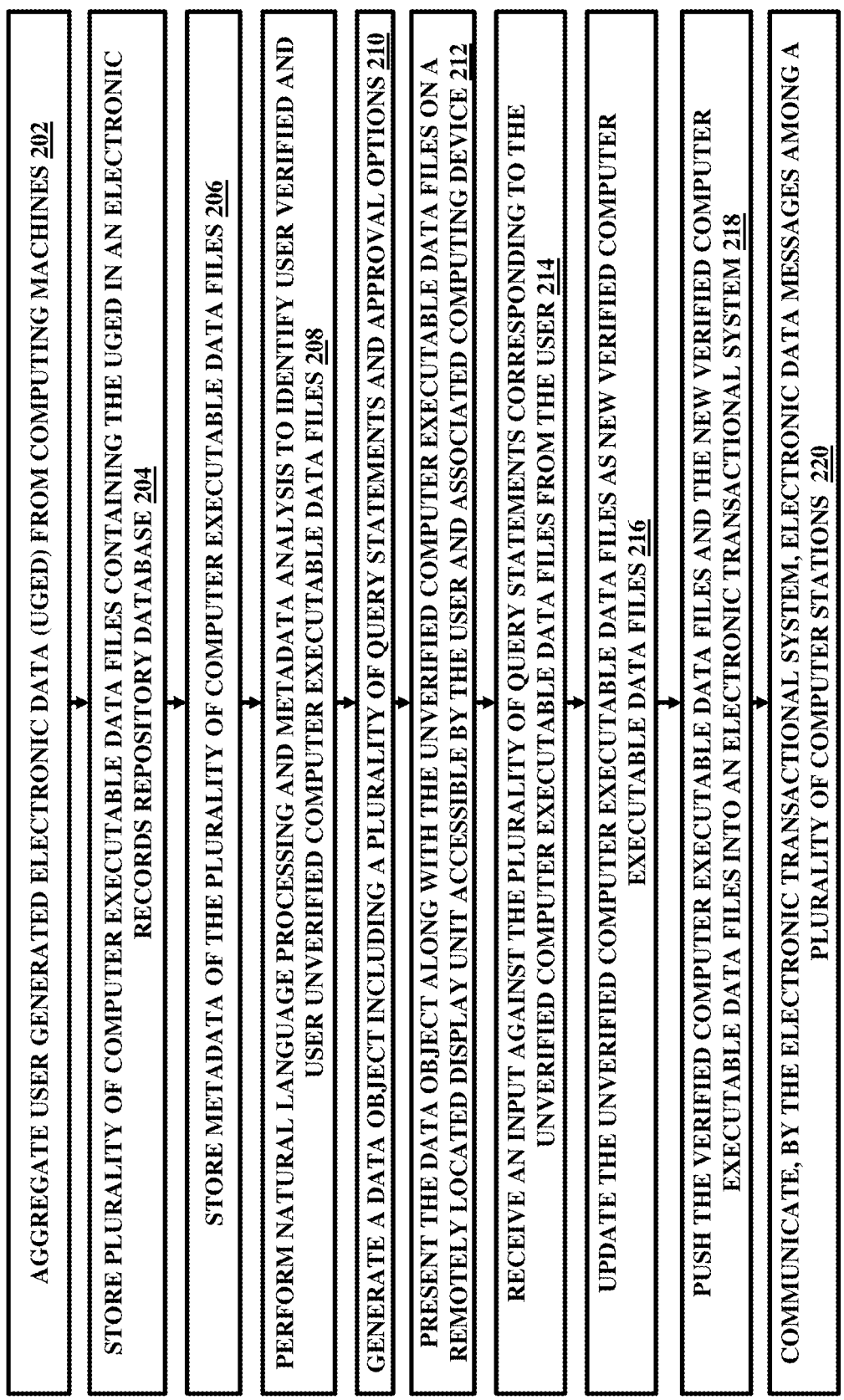
FIG. 2 illustrates a method for integration of the UGED in accordance with an embodiment herein.

FIG. 2, with reference to FIG. 1, illustrates a method flowchart for integration of User Generated Electronic Data (UGED) aggregated from the plurality of computing machines 104a-104c at service provider or at other places in the electronic transactional system 116. The method may be implemented with the use of a computer system (such as system 500 of FIG. 6). At step 202, the method includes aggregating the UGED associated with the user from the plurality of computing machines 104a-104c that may be located separately from one another and remote from the cloud gateway agent server 102. The UGED is aggregated by the cloud agent gateway server 102 from the plurality of computing machines 104a-104c over a network through a communication circuit without user intervention such that the UGED contained in the computer executable data files aggregated from the computing machines 104a-104c is not entered by or sourced from the user directly. The user is not authorized to enter the UGED so as to ensure reliability of the UGED for technical interpretation. Instead, the UGED is aggregated from the plurality of computing machines 104a-104c located at for example service provider as discussed above or aggregated from the devices or wearables and the UGED is later routed to the user for verification upon identification of the unverified computer executable data files as discussed herein.

At step 204, the method includes storing the plurality of computer executable data files in the electronic record repository database 106 communicatively coupled with the cloud gateway agent server 102. At step 206, the method includes storing the metadata associated with the plurality of computer executable data files in the electronic record repository database 106.

At step 208, the method includes performing natural language processing and metadata analysis of the plurality of computer executable data files by the processing circuit 108 that is communicatively coupled with the cloud gateway agent server 102 to identify user verified computer executable data files and user unverified computer executable data files from among the plurality of computer executable user data files. At step 210, the method includes generating, by the processing circuit 108, the data object including the plurality of query statements and approval options corresponding to each of the unverified computer executable user data files.

At step 212, the data object is presented along with the unverified computer executable data files on the remotely located display unit 114 that is accessible by the user upon receipt of an automatically generated notification by the processing circuit 108. The data object may represent an integrated view of the UGED residing on the plurality of computing machines 104a-104c. In an example, the data object may represent an integrated view of a portion of the UGED contained in the unverified computer executable user data files.

At step 214, the cloud agent gateway server 102 receives an input against each of the plurality of query statements corresponding to the unverified computer executable data files by the user. The user input may signify reliability and trustworthiness of the unverified computer executable data files and the UGED contained therein and is indicative of whether the UGED contained in the unverified computer executable data files belongs to the user or not, is correctly attributed to the user or not, is complete or not. A step 216, the unverified computer executable data files are updated as new verified computer executable data files in the electronic records repository database 106 based on the received input. In an example, only those verified computer executable files are updated in the electronic records repository database 106 for which the user verifies the UGED as correctly attributed to the user and/or is complete. In an example, each of the unverified computer executable data files may be updated with indicators indicative of which portion of the UGED is verified by the user as complete, correctly attributed and which portion is incomplete and/or wrongly attributed to the user.

In an example, after receiving user verification or dispute or missing data, the electronic records repository database 106 may update the verification or dispute or the missing data with confirmation or verification flags or indicators or such as verified, unverified, complete, incomplete, and the like. In an example, the external computing machine 112 can supply natural text as comments on top of the flags or indicators for example approved with comments, disapproved with explanation, and the like. If the source of the UGED is known, a message may be sent to the source to make corrections and updates accordingly.

At step 218, the verified computer executable data files and the new verified computer executable data files are pushed into the electronic transactional system 116. At step 220, the electronic transactional system 116 may communicate electronic data messages containing information retrieved from the user verified computer executable data files and the new verified computer executable data files among the plurality of computer stations 118 located at users, service providers, and other entities. The electronic data messages may be communicated only after it is authorized by users who own data contained in the electronic data messages to share the data with one or more of the plurality of computer stations 118.

In an example, the UGED may be derived from a plurality of sources such as the plurality of computing machines 104a-104c including such as without limitations a plurality of user-driven or user-associated devices at a hospital or at a service provider. The devices may, for example, include devices to track exercise routines, diet management systems, fitness trackers, weight tracking devices, etc., without limitations. The devices may also include, for example, wearables (e.g., wearable devices).

The UGED may be stored in a UGED repository associated with each of the plurality of computing machines 104a-104c from where the UGED may be collected by the cloud agent gateway server 102.

In an example, the electronic transactional system 116 may include an electronic record of user information that can be created, gathered, managed, and consulted by authorized clinicians or other professionals and staff of a specific service provider that creates the record. The electronic transactional system 116 may also house an electronic record of user information that conforms to nationally recognized interoperability standards and that can be created, managed, and consulted by authorized clinicians and staff of the service provider that creates the record as well as those at other service provider sites. Accordingly, the electronic transactional system 116 may be aimed at an efficient management of multiple records in a single service provider's practice, and integrating multiple data sources into each electronic record.

The electronic transactional system 116 may house a complete history of many users collected from a variety of sources including professionals or staff at hospitals, clinics, and laboratories communicating through standard networks. The electronic transactional system 116 may also include biographical information about the user describing the user, including but not limited to the user's age, gender, height and weight, and history information including the user's conditions, previous procedures, medications, and laboratory test results. The electronic transactional system 116 may also integrate devices data that are representative of the user's routines and diagnostics, etc. The electronic transactional system 116 may be centrally accessed by many different sources and thus serves as a path of intercommunication among many individuals and machines working together to deliver a service.

The embodiments herein may allow aggregating of the UGED from a plurality of sources including user-driven or user associated devices so as to integrate devices data into the electronic transactional system 116. In some embodiments, a portion of the aggregated UGED may be already approved by a user or a professional while another portion of the UGED may not be approved by either a user or a professional. In such cases, it is important to recognize the portion of the UGED that is not approved by either of the user or the professional. The embodiments herein may allow applying metadata analysis and natural language processing to evaluate the portion of the UGED that is not approved and requires an approval. The UGED aggregated from the plurality of sources or the plurality of computing machines 104a-104c may include diverse and heterogeneous formats and types.

The UGED may be homogenized by the processing circuit 108. The process of homogenization may include standardizing the heterogeneous and diverse UGED so as to define it in compliance with a standard format or type as prescribed by the electronic transactional system 116 before its integration. The processing circuit 108 may be configured to homogenize the UGED contained in the computer executable data files in a defined standard compliant format, for example. The embodiments herein may allow harmonizing and categorizing data that needs approval based on the evaluation. The process of harmonization and categorization identifies which portion of the UGED needs approval from a user and which portion of the UGED needs approval from which professional. In an example, the embodiments herein may further allow processing of a user approval, wherein an approval is requested from the user associated with the UGED. The user approval may signify one or more of accuracy of the UGED, reliability of the UGED, completeness of the UGED, and defines a person responsible for accuracy and completeness of the UGED who may be either the user himself, a relative of the user, a professional, or any other person or firm. In some embodiments, the user may be a child or any other person who may not act for approval by himself. In such cases, an advocate may be assigned to approve or verify the data on behalf of the user. The user advocate may approve the aggregated data in such embodiments and a user advocate approval may be processed instead of a direct user approval processing. For example, a parent of a child may be considered as a user advocate in some cases.

In an example, the embodiments herein may allow processing a professional approval. The professional approval signifies one or more of accuracy of the UGED, reliability of the UGED, completeness of the UGED, and defines a person responsible for accuracy and completeness of the UGED who may be either the user, a relative of the user, the professional, or any other person or firm. The subsequent approval by the professional after the user approval facilitates in providing an increased degree of trust and reliability of the UGED for assisting in workflow during decision making. The multi-level approval by the user himself and subsequently by the authorized professional is maintained in the electronic transactional system 116 with a reliability index determined based on the approval from the professional and/or the user. The reliability index is indicative of a degree of accuracy and completeness and trustworthiness of the UGED aggregated from the plurality of computing machines 104a-104c.

In an example, the reliability index of the UGED may be determined before integration of the UGED into the electronic transactional system 116. If the UGED is identified to be verified by the user (Yes), then a first trust score is associated with the aggregated UGED. Otherwise, if the UGED is identified to be not verified by the user (No), then a second trust score is associated with the aggregated UGED. The second trust score is different from the first trust score. In an example, based on the user input through one of the approval options signifying verification status, the processing circuit may associate a numerical trust score with each of the new verified computer executable data files.

Subsequently, it may be determined whether the aggregated UGED is approved by a professional. If the UGED is identified to be verified by the professional (Yes), then a third trust score is associated with the aggregated UGED. Otherwise, if the aggregated UGED is identified to be not approved by the professional (No), then a fourth trust score is associated with the UGED. The fourth trust score is different from the third trust score. In some embodiments, the user may be a child or any other person who may not act for verification by himself. In such cases, an advocate may be assigned to verify the UGED or a computer executable user data file on behalf of the user. The user advocate may verify the aggregated data in such embodiments and user advocate verification may be processed instead of a direct user verification processing. For example, a parent of a child may be considered as a user advocate in some cases. Based on whether an advocate is needed or not, the verification may be requested by the user or by his advocate.

The UGED may be associated with a cumulative score based on identified scores form among the first trust score, second trust score, third trust score, and the fourth trust score to generate the reliability index for the UGED. For example, if the UGED or any of the unverified computer executable data files is verified by the user as well as the professional, then the cumulative score associated with the UGED or the unverified computer executable data file is defined based on the first trust score and the second trust score. If the UGED is approved by the user but not by the professional, then the cumulative score is defined based on the first trust score and the fourth trust score. If the UGED is approved by the professional and not by the user, then the cumulative score is defined based on the second trust score and the third trust score. If the UGED is approved by neither the user not the professional, then the cumulative score is defined based on the second trust score and the fourth trust score.

With the use of the reliability index and the cumulative scores associated with the UGED and the multi-level verifications/approvals of the UGED, the accuracy, completeness, and validity of the multi-sourced UGED may be assessed. Based on the assessment, appropriate and accurate decisions can be made.

The UGED may be pushed into the electronic transactional system 116 which may be accessed by other parties associated with the plurality of computing stations 112. In accordance with various embodiments herein, the UGED gathered from the plurality of computing machines 104a-104c may be verified for accuracy and therefore the professionals or other parties accessing the UGED through the electronic transactional system 116 can identify which portions of the UGED are accurate and which are not and accordingly use the accurate and verified portions of the UGED for decisions and users' management solutions.

The communications transmitter 120 may be configured to receive requests for accessing the UGED by a party authorized to access the electronic transactional system 116 and/or send output data to the party in response to the access. The communications transmitter 116 may be enabled through a communication channel such as the Internet, and including a wired or a wireless or both communication mediums.

The embodiments herein may facilitate multi-source unverified user generated data collection and integration within the electronic transactional system 116. The embodiments herein may further allow processing of validity and approval of the unverified user generated data files so as to promote reliable decision making. The multi-level approval techniques and systems ensure high reliability and validity. The systems and methods provided by the embodiments herein allow verification and approval of the UGED.

In some embodiments, authorized parties may be notified by the electronic transactional system 116 of the aggregated and verified UGED so that the authorized parties can access portions of the UGED for use in workflows with sufficient level of trust and confidence. Notifications may be sent on a periodic basis or when there is an update in the electronic transactional system 116. In an embodiment, users who are respective owners of the UGED may also be informed through notifications about access of the UGED by the authorized parties or about requests for authorizations by unauthorized parties for seeking user approval(s) of access to the UGED.

In some embodiments, when the UGED is pushed into the electronic transactional system 116, it may also include details about who is authorized to view the UGED. A user may allow an authorized party to further authorize access to more persons or entities based on defined conditions. For example, a professional authorized to access UGED by a user may be allowed by the user to further share the data with a neurologist whom the professional needs to consult for diagnosis. An interface (not shown) may be provided to share the data to more persons or parties. In some embodiments, customized actions and reactions may be defined by setting defined rules for facilitating implementation of behavioral patterns through specific triggers.

In an example, the embodiments herein allow one to discover anomalies in the UGED such that someone in an entire supply chain does not make a wrong decision utilizing the wrong UGED through the electronic transactional system 116. The embodiments herein allow increasing and/or identifying reliability of the UGED through associated scores based on who has verified the UGED. The embodiments herein enable a user to intervene in data management process of the electronic transactional system 116 thereby improving reliability and trustworthiness of the UGED. Thus, the electronic transactional system 116 may confirm to others using the UGED as to how much the UGED can be trusted for various end purposes.

In accordance with various embodiments, the electronic transactional system 116 is designed to include user-centric features so as to address user verification challenges that remain missing if the UGED utilized through the electronic transactional system 116 is not verified by the user. The electronic transactional system 116 not only is networked to the service provider but also to the user directly and indirectly through other servers in different embodiments. The embodiments herein provide a facility to let the user intervene for confirmation of or dispute with the UGED used by the electronic transactional system 116. The electronic transactional system 116 may employ a plurality of user-centric applications to facilitate interaction with users. An exemplary electronic transactional system 116 is shown in FIG. 3, with reference to FIGS. 1 through 2. The electronic transactional system 116 is networked with the cloud gateway agent server 102 as well as the plurality of computing stations 112 for access of the UGED contained in the computer executable user data files. The electronic transactional system 116 may include or coupled with the communications transmitter 120. The communications transmitter 120 may facilitate transmitting of the data messages as discussed above as well as transmission and receipt of the verified computer executable data files and the new user verified computer executable data files from the cloud gateway agent server 102. The electronic transactional system 116 may further include a rules repository 302 to store verification rules that define standard guidelines for accepting and/or rejecting the computer executable data files based on a trust score associated with the computer executable data files received from the cloud gateway agent server 102. The electronic transactional system 116 may further include a filter circuit 304 capable of automatically separating a computer executable data file that does not meet criteria as defined by the verification rules and rejects the computer executable data file from being pushed into the electronic transactional system 116 if the trust score associated with the computer executable data file is below a threshold limit. The electronic transactional system 116 may include the data storage device 306 for storing the UGED in the form of computer executable user data files. The electronic transactional system 116 may include a processor 308 for executing programmed instructions associated with the electronic transactional system 116. The electronic transactional system 116 may include an interface unit 310 capable of providing an interface for communication between the electronic transactional system 116 and the cloud gateway agent server 102.

The electronic transactional system 116 further includes an Electronic Record (ER) data server 312. Among other tasks, the ER data server 312 in association with the processor 308 and social networking applications 314 may be configured to execute programmed instructions for enabling social linkages with various entities such as users, service providers and other entities through a socially aware network or social networking platform. The social networking applications 314 may allow for storing and creating electronic records, and authorizing access to a third-party computer such as the computing station 112 to the electronic records through the social networking platform with dynamically changing connections wherein, the third-party computer is associated with the social networking platform as a dynamically changing connection. A user computer or a third-party computer may also be associated as a dynamically changing connection with the social networking platform. The computing station 112 may be communicatively connected to the electronic transactional system 116 through the social networking platform as a dynamically changing connection and the ER data server 312 may serve as a component of the social networking platform. The social networking platform herein may refer to a socially networked engine or portal allowing access to a crowd of persons or computers as network connections whose identity and profile and social relationships among one another changes dynamically over time. These dynamically changing connections may access the electronic transactional system 116 through registered social profiles. The social networking platform may allow users (who are registered as dynamic connections) to sign up and communicate with their friends, peers, colleagues, coworkers or other individuals they share some common interest with. These connections are made through requests and most commonly must be mutually accepted before certain functionality is allowed between two or more individuals. The connections provide the ability to the users to share content amongst and between them through the electronic transactional system 116 enabled through the social networking applications 314.

In an example, the electronic transactional system 116 may be deployed as a social networking server for data interactions and UGED exchange with the computing stations 112 through social profiles of various entities associated with the computing stations 112. The social networking applications 314 may be enabled through a social networking module 316 which supports standard social networking operations such as hosting of social profiles and/or accessing of social profiles of the various entities, and facilitating communication among the entities through the electronic transactional system 116 as a social networking server. The entities may request to access the UGED. In return, the electronic transactional system 116 may generate and supply to the entities an entity-controlled social profile. The entity-controlled social profile page may include a web link that may redirect a computing station such as 118 to the requested UGED or requested computer executable data file. In accordance with this embodiment, the UGED may be accessed through the social networking platform as the social networking platform is networked to the electronic transactional system 116 and/or deployed through the electronic transactional system 116.

Figure 4:
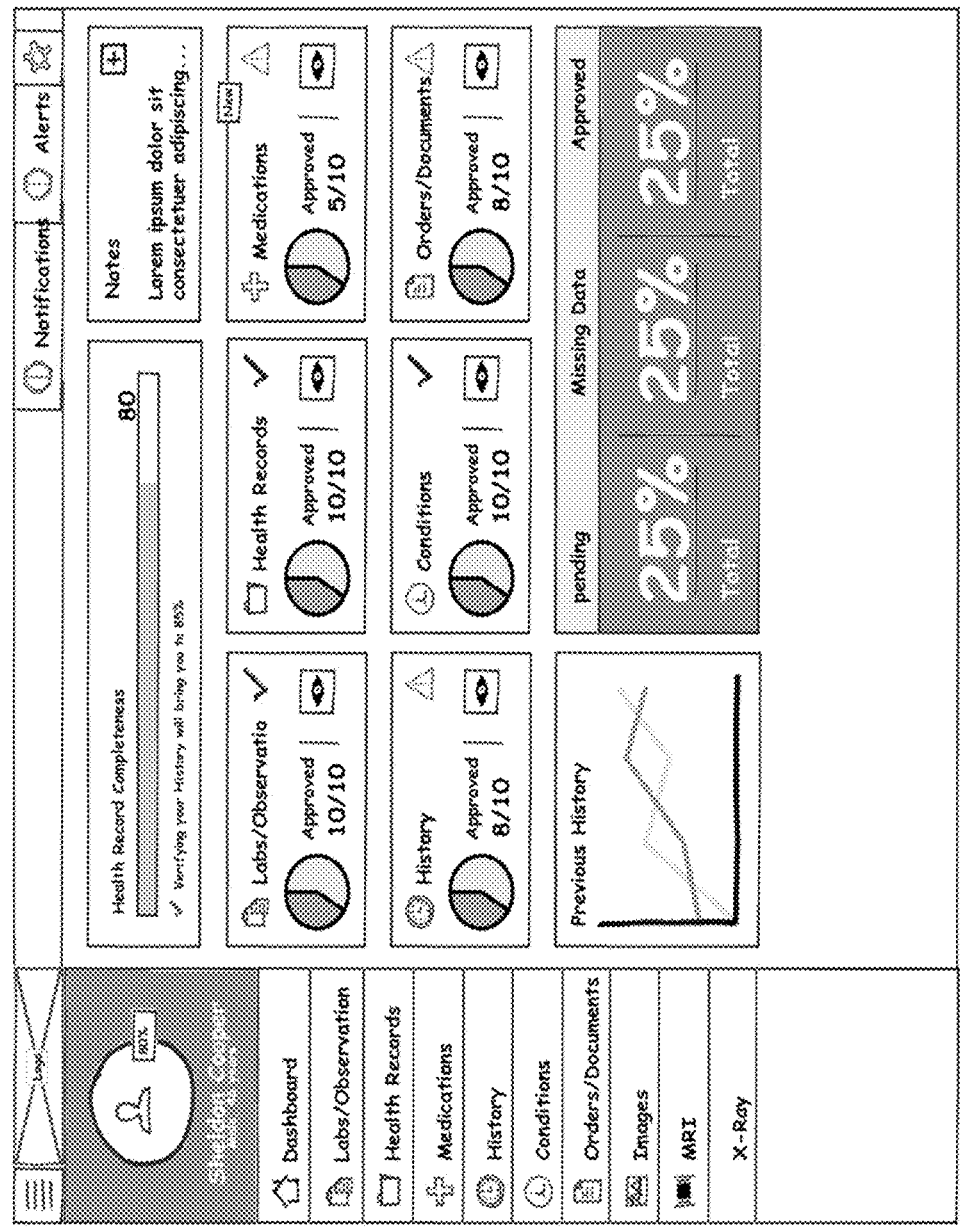
FIGS. 4 and 5 illustrate exemplary user interfaces for allowing a user to interact with a cloud gateway agent server for verification of the UGED in accordance with the embodiments herein.
Figure 5:
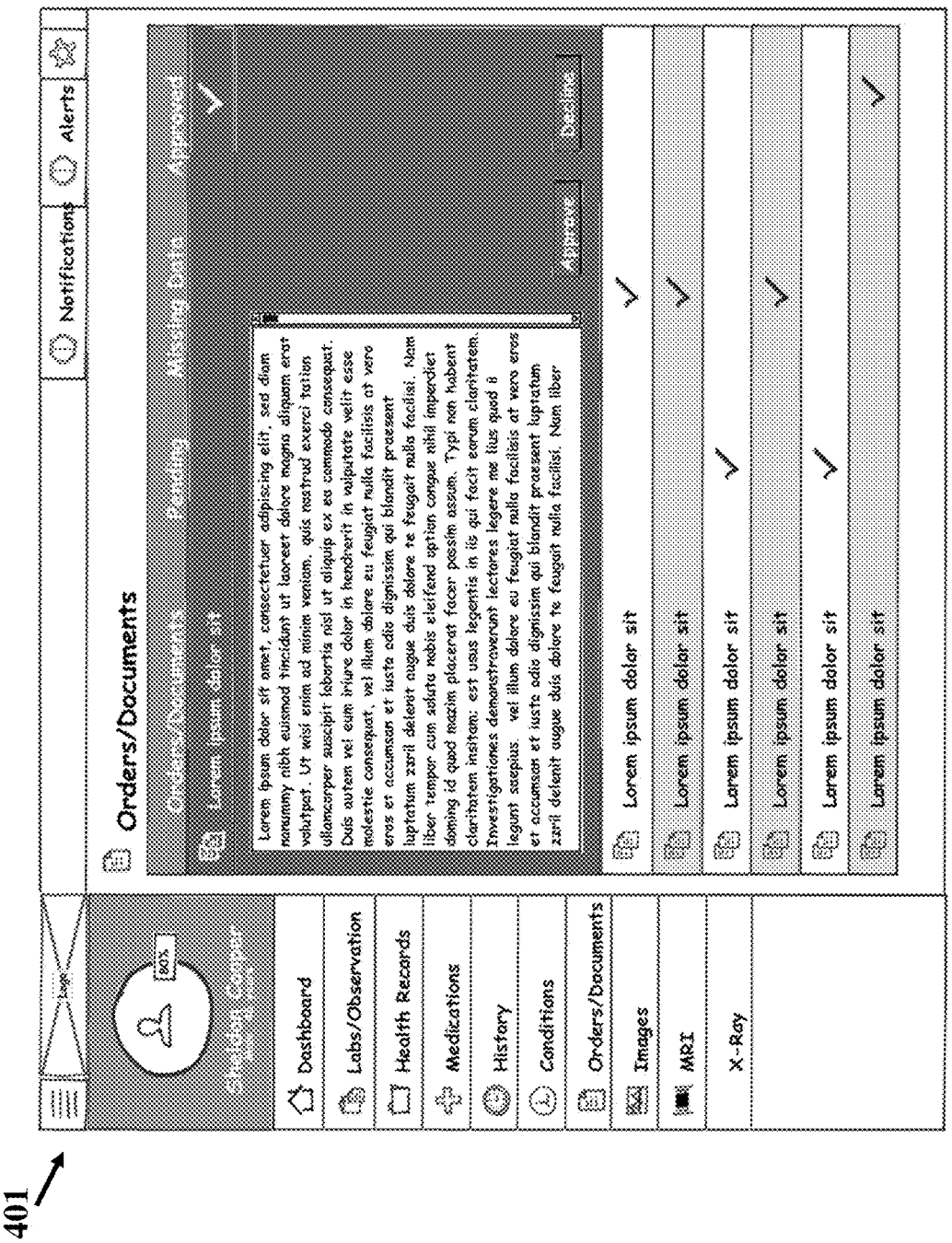

FIG. 4, with reference to FIGS. 1 through 3, illustrates a user interface 400 for a user presented to the display unit 114 upon launching of the gateway application 124*a*. The data object transmitted from the cloud gateway agent server 102 may enable presenting of the query statements and the verification options or approval options to the user as depicted in the exemplary user interface 400. The user may receive notification and alerts about new unverified computer executable data files aggregated by the cloud gateway agent server 102. The status of the plurality of computer executable data files may be reflected under different classes such as labs related, other records, medications, and the like. The data object may also reflect number of electronic data files that are verified/approved, that are unverified/pending for verification and that are missing or incomplete etc. As shown in FIG. 5, with reference to FIGS. 1 through 4, a new user interface 401 may be presented to the user upon selection of a particular unverified computer executable data file. The user can review text embedded in the unverified computer executable data file and through a single-click option may either decline the unverified computer executable data file indicating that data contained therein is wrong or may accept it indicating that the data contained is verified by the user.

As shown in FIGS. 4 and 5, the user interfaces 400, 401 may provide an integrated view of the unverified computer executable data files such that the user may find entire unverified UGED at a single place in a structured manner and the user may have to merely select a particular data file and either verify the UGED contained therein or dispute it by a single clickable approval option. The user may review from a single screen all the unverified computer executable data files and locate sources from where the UGED contained in the different computer executable files are derived. The data object transmitted from the cloud gateway agent server may define the unverified UGED in a structured and unified manner before being presented to the computing machine 104*a*.

In an example, the data object may contain the query statements such as whether the data is correct or not, whether the data is complete or not, whether the specific physiological conditions mentioned in a computer executable data file are correct or not, and the like. The data object may also include a plurality of single-clickable approval options as discussed above. The data object may also contain embedded digital text-based notes for presentation to the user on the user interface upon launch of the gateway application 124*a*.

In an example, the cloud gateway agent server 102 may manage UGED overload by for example classifying the UGED into solicited and unsolicited information based on instructions from professionals, service providers or from other entities that use the UGED through the electronic transactional system 116. The cloud gateway agent server 102 may prioritize review of the UGED by users in accordance with whether the UGED contains the solicited information or the unsolicited information. The solicited information may include information requested by a computing station such as the computing station 118 associated with an entity for use and as such may be prioritized for users review by the cloud gateway agent server 102. The unsolicited information on the contrary may not have been demanded or requested by an entity and accordingly review of the unsolicited information may be delayed. The entities may send a request to the electronic transactional system 116 about what they need and accordingly the electronic transactional system 116 may communicate this to the cloud gateway agent server 102 and the cloud gateway agent server 102 may accordingly classify the UGED and prioritize the review for the solicited information. The entities may determine what type of data may be useful to them in informing diagnosis and treatment decisions and the cloud gateway agent server 102 may prioritize the review based on what is determined to be useful by the entities associated with the computing stations 118.

Figure 6:
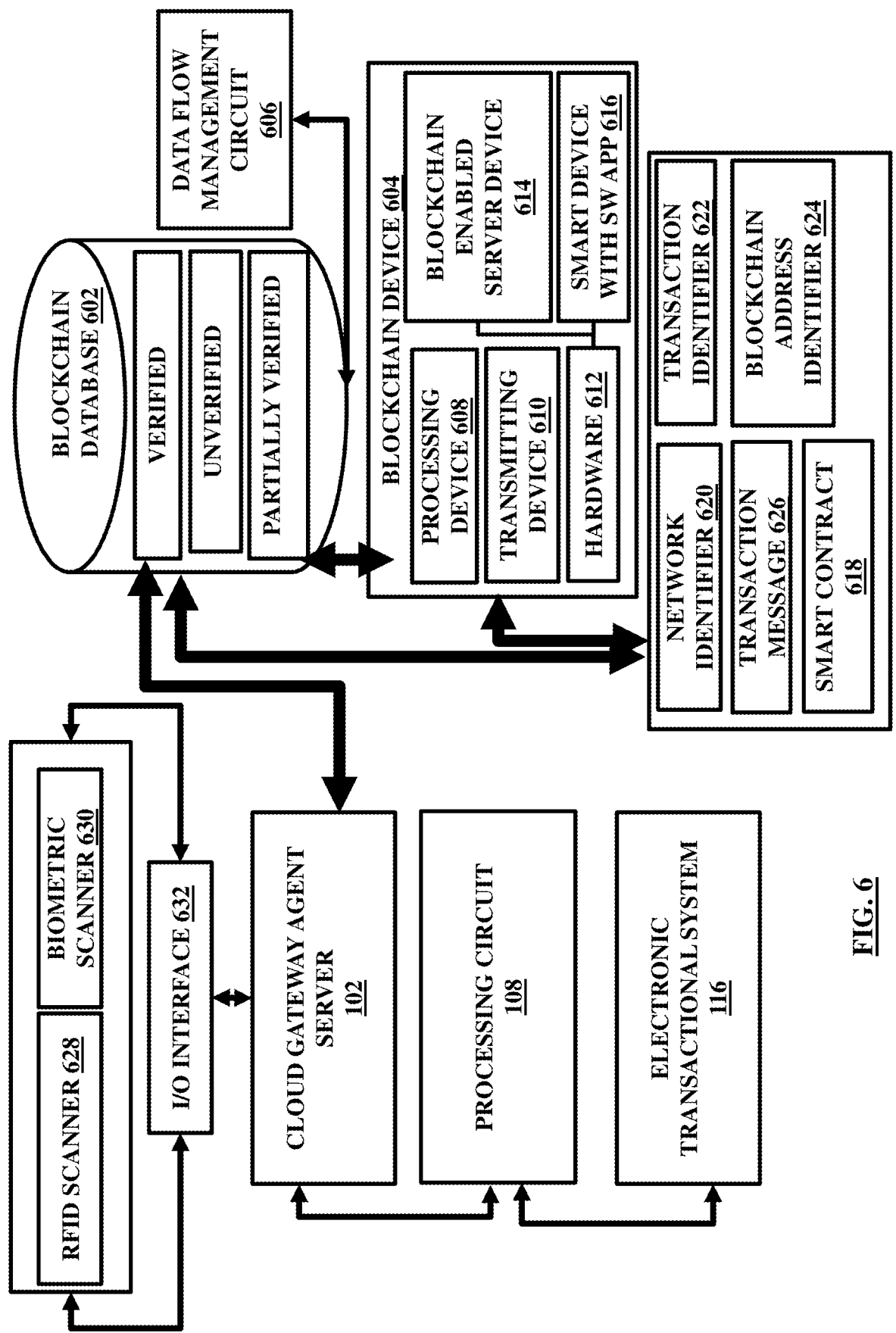
FIG. 6 illustrates the cloud gateway agent server and the electronic transactional system connected together and with other devices in a blockchain environment in accordance with the embodiments herein.

FIG. 6, with reference to FIGS. 1 through 5, illustrates the cloud gateway agent server 102 and the electronic transactional system 116 connected together and with other devices in a blockchain environment. As shown, the blockchain environment includes a blockchain database 602 and a blockchain device 604 that are communicatively coupled to one or more of the processing circuit 108, cloud gateway agent server 102, and the electronic transactional system 116.

In an embodiment, the blockchain database 602 may be communicatively and operatively coupled with the cloud gateway agent server 102 to store the plurality of computer executable data files and metadata associated with the plurality of computer executable electronic data files. The metadata associated with the plurality of computer executable data files may be indicative of details about the user, such as name, age, gender, user verification status, and the like as discussed in conjunction with FIG. 1. The blockchain database 602 may store the UGED contained in the plurality of computer executable data files.

The computer executable data files may be received on-demand by the cloud gateway agent server 102 from the plurality of computing machines 104*a*-104*c* and accordingly pushed into the blockchain database 602. A data flow management circuit 606 may be coupled with the blockchain database 602 and the cloud gateway agent server 102 to control flow of the computer executable data files from the plurality of computing machines 104*a*-104*c* on-demand by the cloud gateway agent server 102.

The processing circuit 108 is coupled communicatively and operatively with the cloud gateway agent server 102 and the blockchain database 602. The processing circuit 108 is configured to perform natural language processing and metadata analysis of the plurality of computer executable data files to identify user verified computer executable data files and user unverified computer executable data files from among the plurality of computer executable data files aggregated from the plurality of computing machines 104*a*-104*c* in a manner as discussed in conjunction with FIG. 1. The processing circuit 108 may include or be coupled communicatively and operatively with the rules engine 110 as shown in FIG. 1 to perform tasks as discussed in conjunction with FIG. 1.

In an embodiment, the blockchain database 602 may replace the electronic records repository database 106 while performing all functions of the electronic records repository database 106 along with additional blockchain capabilities and functions. In some embodiments, however, the electronic records repository database 106 and the blockchain database 602 can both be included in the blockchain environment to simultaneously perform their respective tasks in the same environment.

The blockchain database 602 may store the UGED contained in the form of computer executable data files. The blockchain database 602 also stores classified files in the form of verified UGED, unverified UGED, and partially verified UGED contained in the respective verified computer executable data files, unverified computer executable data files, and partially verified computer executable data files.

The processing circuit 108 may update the unverified computer executable data files and partially verified computer executable data files as new verified computer executable data files in the blockchain database 602 based on the input received from a user or an associated computing device signifying verification of the unverified computer executable data and the partially verified computer executable data files by the user. The new verified computer executable data files may include data elements that may be identified as accurate and belonging to the user as indicated by the user input, or may include data elements that may be identified as inaccurate and not belonging to the user as indicated by the user input or a combination of both. Even if the data elements are not accurate or complete which may represent that all or a portion of the UGED does not belong to the user and is wrongly attributed to the user or is incomplete, the UGED or a portion thereof is still considered as verified but wrong or incomplete data. These details may be maintained and stored in the blockchain database 602. The processor or processing circuit 108 may allow storing the unverified computer executable data files and the partially verified computer executable data files as the new verified computer executable data files in the blockchain database 602 with the first indicator if the input is indicative of the user generated electronic data contained in the unverified computer executable data files to be reliable and belonging or rightly attributed to the user. The processing circuit 108 may allow storing of the unverified computer executable data files and the partially verified computer executable data files as the new verified computer executable data files in the blockchain database 602 with the second indicator if the input is indicative of the UGED contained in the unverified computer executable data files and/or the partially verified computer executable data files to be non-reliable and not belonging to the user and wrongly attributed to the user. The processing circuit 108 may also allow to store the first indicator and the second indicator along with the new verified computer executable data files such that the first indicator and the second indicator can facilitate in categorization of the verified and the unverified data and reliable or non-reliable UGED in future once more user generated electronic data comes in and gets aggregated by the cloud gateway agent server 102 in the blockchain database 602.

The blockchain device 604 may include a processing device 608 and a transmitting device 610 that each is capable of blockchain integration unlike generic devices. The processing device 608 may process all blockchain tasks through computer-controlled software and hardware tools. The transmitting device 610 can allow transmission of information such as but not limited to the UGED and respective computer executable data files from the blockchain database 602 to the processing circuit 108, cloud gateway agent server 102 and the electronic transactional system 116. The transmitting device 610 may also enable all sorts of communication with various systems and devices including the cloud gateway agent server 102 and the electronic transactional system 116.

In an embodiment, the blockchain device 604 may store image-based input received from an image recognition device, voice-based input received from a microphone, location coordinates received from a global positioning system (GPS), other sound/video characteristics received from such as intelligent sound and video recording devices etc in order to perform verification of identity of the user or owner of the UGED at least in part. These devices are discussed below in conjunction with FIG. 7.

The blockchain device 602 also includes hardware 612. The hardware 612 may comprise a specific blockchain-enabled server device 614 and a smart device 616 running a specific dedicated software application operated by a person. The smart device 616 is configured to engage in specific communication with the blockchain-enabled server device 614. The blockchain-enabled server device 614 performs tasks enabling communication with the smart device 616. The blockchain-enabled server device 614 further performs at least one of these tasks: storage of at least one data base or a portion thereof and/or data for placement therein in the blockchain database 602, access the at least one data base including the blockchain database 602, update the at least one database including the blockchain database 602, allow the smart device 616 to access and receive information in whole or in part from the at least one database. In some embodiments, the at least one data base such as the blockchain database 602 may contain at least one unique hash, at least one timestamp of the at least one unique hash, and/or other data for generating smart contracts such as a smart contract 618.

The transmitting device 610 may allow transmission of at least one hash file and/or hash blockchain to the blockchain-enabled server 614. The transmitting device 610 may further allow receiving a transaction confirmation and/or identifier from the smart device 616, creating a hash file and/or hash blockchain from the digital data and/or digital content, receiving the hash file and/or hash blockchain and the timestamp from the smart device 616. The processing device 608 may compare the hash file and/or hash blockchain to other verification information for verifying authenticity of a variety of information.

The processing device 608 may generate a network identifier 620, a transaction identifier 622, and a blockchain address identifier 624 to specify a particular transaction that involves aggregation o UGED in the form of one or more computer executable data files associated with one or more users who own the UGED at least in part. Each such set of identifiers define a specific transaction indicated through a smart contract such as the smart contract 618 that cannot be tempered. The smart contract 618 allows tracing the aggregation of the UGED and the respective computer executable data files as well as verification of the computer executable data files for any particular transaction involving a verification of the computer executable data files. In an embodiment, the processing device 608 is configured to cause the smart contract 618 to be generated based on the network identifier 620, transaction identifier 622, and the blockchain address identifier 624 such that the smart contract 618 is configured to automatically validate a transaction using a special key associated with a user or a transaction.

A transaction message 626 may be generated by the processing device 608 to inform respective entities such as the owners of the UGED at least in part indicative through one or more computer executable data files, a verifying authority etc. In an embodiment, the transaction message 626 may be associated with one or more secured hash links so that the transaction message 626 is generated when the one or more secured hash links are activated and the respective computer executable data files are stored in the blockchain database 602.

The processing device 608 may generate the network identifier 620 that may be associated with a blockchain network and the transaction ID (identifier) 622. The processing device 608 may generate the blockchain address identifier 624 using at least a unique key included in a transaction request and one or more hashing codes including verification details associated with the respective user (owner of one or more computer executable data files or owner of UGED at least in part).

In an embodiment, the blockchain address identifier 624 may be based on a public key corresponding to a private key that was used to register the transaction on the blockchain such that the public key and the private key are part of a public/private key pair associated with the transaction indicative of the verification of the one or more of the computer executable data files.

The transmitting device 610 may be configured to transmit the transaction message 626 to the user (such as a respective computing device) and the verifying authority (such as including the electronic transactional system 116 and/or the processing circuit 108 or other verification devices as discussed later), and a respective computing station such as the computing station 118*a* for private use.

Figure 7:
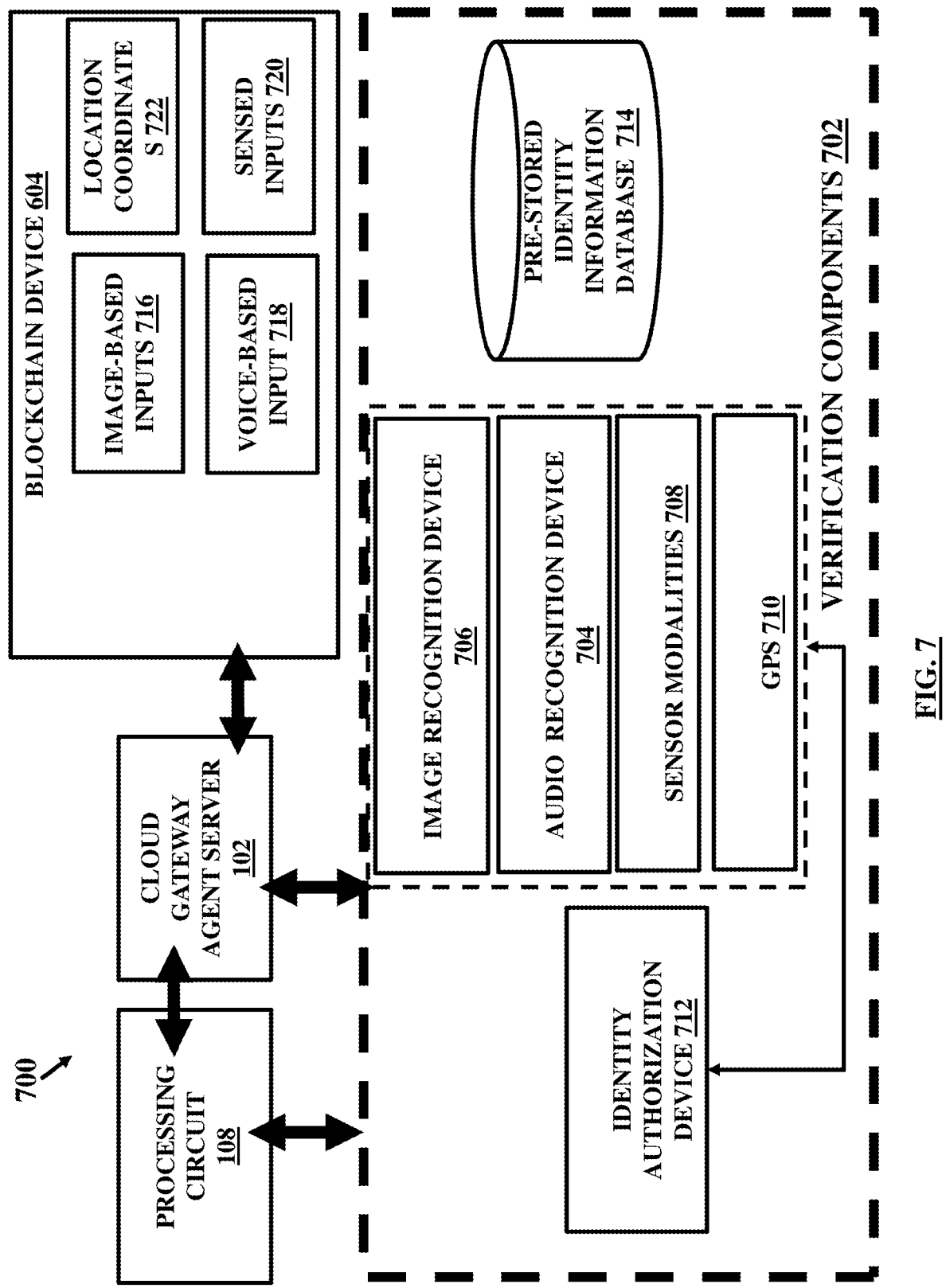
FIG. 7 illustrates the cloud gateway agent server and the processing circuit among other components in accordance with the embodiments herein.

FIG. 7, with reference to FIGS. 1 through 6, illustrates a system 700 comprising the cloud gateway agent server 102 and the processing circuit 108 among other components according to an embodiment herein. As shown in FIG. 7, the processing circuit 108 may include or be coupled to verification components 702. The verification components 702 may include an audio recognition device or voice recognition device 704, an image recognition device 706, sensor modalities 708 including a GPS 710, and identity authorization device 712. The GPS 710, the audio recognition device 704, the image recognition device 706, other sensor modalities 708, and the identity authorization device 712 together may be termed as verification components. The processing circuit 108 along with the verification components 702 may together be employed to perform verification of the user who owns the UGED at least in part indicative of owned electronic records verified or not verified or partially verified by the user and contained in one or more of the computer executable data files.

The verification components 702 may be coupled communicatively with the processing circuit 108. The verification components 702 and/or the processing circuit 108 may be coupled to a pre-stored identity information database 714 that is used to store identity information of a plurality of users and their associated computing devices who owns the UGED at least in part.

The verification components 702 may include the identity authorization device 712 for verifying identity of the plurality of computing devices of the users who associate themselves as owners of the UGED at least in part. In some embodiments, the identity authorization device 712 may include the voice or audio recognition device 704, the image recognition device 706, and the sensor modalities 708 which are discussed later in the document. In some embodiments, the identity authorization device 712 may not include but may be operatively and/or communicatively coupled to the voice or audio recognition device 704, the image recognition device 706, and the sensor modalities 708.

The identity authorization device 712 may include other necessary components that are blockchain configured and allow authenticating and/or verifying the computing devices (and associated users) by allowing them access to the unverified computer executable files and the partially verified computer executable files and associated repositories based on access privileges upon verification of their respective identity information by the identity authorization device 712.

In accordance with the embodiments discussed herein, the identity authorization device 712 may authenticate a user and an associated computing device to access the unverified computer executable files and the partially verified computer executable files upon verification of its identity information along with its registration information. In an embodiment, the registration information may be identified through the identification information of the computing device and/or the associated user so that separate registration information may need not to be verified prior to allowing access or denial. In an embodiment, however, the registration information may be defined separately and may need to be verified separately in order to gain access to the computer executable files associated with the user.

The audio recognition device 704 may be coupled to the identity authorization device 712 for enabling access upon authorization by the identity authorization device 712. In an embodiment, the identification and authorization of identity of the user and the associated computing device may be established based on voice patterns of the respective user. In an example, in the event the processing circuit 108 does not identify the user based on signals transmitted from the audio recognition device 704 or image recognition device 706, then the processing circuit 108 may initiate a request for the user to enter another voice input, or facial/visual input, etc. into the audio recognition device 704 and/or image recognition device 706, respectively. Upon a predetermined unsuccessful number of attempts by the user of inputting voice signals into the audio recognition device 704 or visual inputs into the image recognition device 706, which the processing circuit 108 fails to recognize, the system 700 may initiate an automatic termination/lock-down mode to prevent any further attempts for the user to access the system 700 through additional voice or visual inputs or other types of inputs. The processing circuit 108 may transmit a user-access denial output signal upon not authenticating an identify of a user. For example, the output signal may be in the form of an audio signal (e.g., voice output indicating "Fail" or buzzer, etc.) or visual signal (e.g., red light, etc.)

Figure 8:
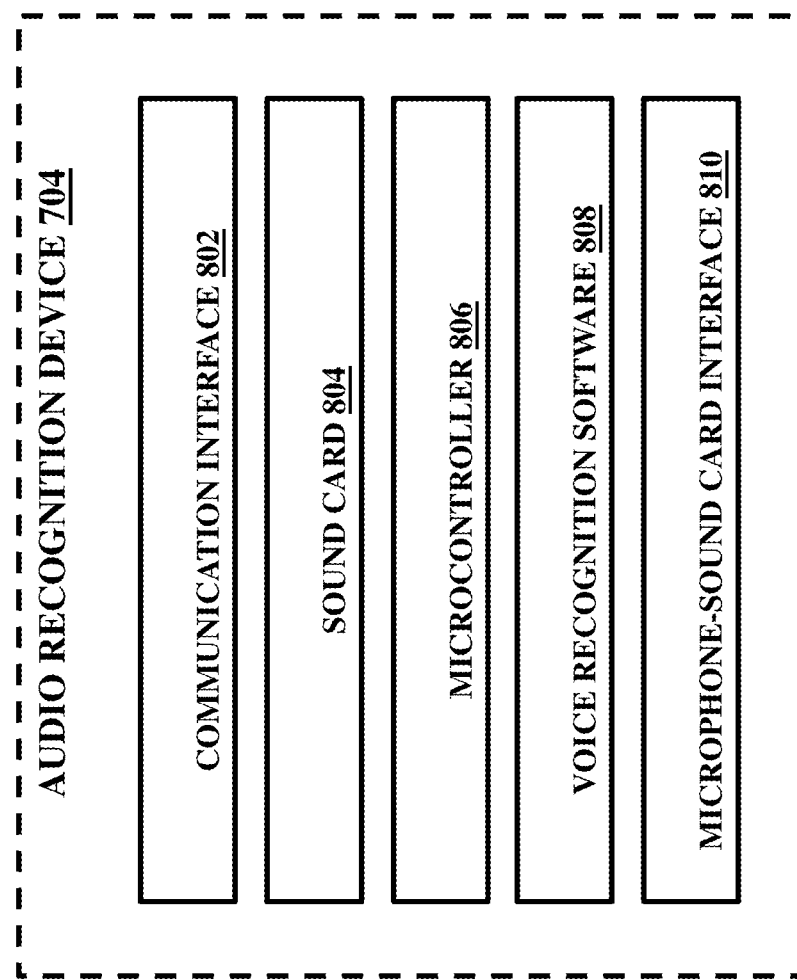
FIG. 8 illustrates an exemplary audio recognition device, in accordance with the embodiments herein.

The audio recognition device 704 may include a communication interface 802, as shown in FIG. 8, with reference to FIGS. 1 through 7, for establishing communication with other devices over a communication network. The audio recognition device may further include a sound card 804. The sound card 804 is adapted to receive identity information of the user. The identity information is received in the form of a digital audio signal. The sound card 804 is adapted to receive the digital audio signal and generate/transmit the audio signal to a microcontroller 806 for voice recognition based on pre-stored voice patterns. The sound card 804 is adapted to sample an analog signal to generate the digital audio signal and interface with the microcontroller 806. The microcontroller 806, in association with voice recognition software 808, is adapted to discriminate between multiple audio patterns and also compare the voice pattern of the user with the pre-stored voice patterns to output a stream signal. The stream signal is indicative of verification of the identity information. If the identity is verified, the user and the associated computing device may be authorized for access and contribute to verify the UGED at least in part and the associated computer executable files. In an embodiment, the audio recognition device 704 may include a microphone-sound card interface 810 for allowing interfacing between an external microphone with the sound card 804 of the audio recognition device 704.

The image recognition device 706 may be communicatively coupled to other verification components. The image recognition device 706 may allow enabling access upon authorization by the identity authorization device 712 based on image analysis. In this embodiment, identification and authorization of the identity of the user and/or the associated computing device may be established based on image patterns of the user.

Figure 9:
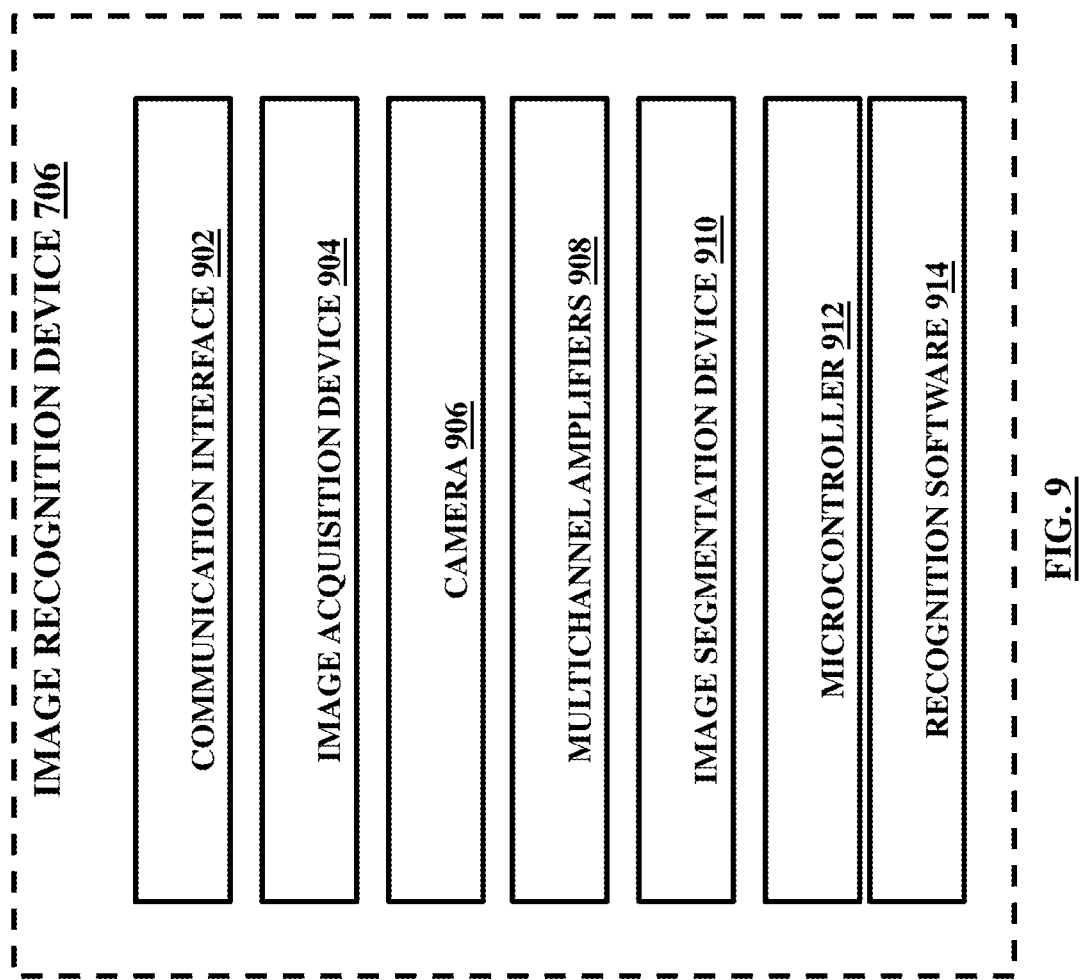
FIG. 9 illustrates an exemplary image recognition device, in accordance with the embodiments herein.

The image recognition device 706 may include a communication interface 902, as shown in FIG. 9, with reference to FIGS. 1 through 8, for establishing communication with other devices over the communication network similar to the communication interface 802 discussed above in conjunction with the audio recognition device 704. The image recognition device 706 is discussed in conjunction with FIGS. 7 and 9 herein.

The image recognition device 706 includes an image acquisition device 904 to receive signals containing image patterns and facial expressions. The image acquisition device 904 may include or be coupled to an external camera 906 for taking still or streaming images. The image acquisition device 904 may include a plurality of multichannel amplifiers 908 such that each amplifier of the multichannel amplifiers 908 may be defined to receive a specific type of sensed information from a particular type of sensor or camera sourcing signals for the image recognition device 706. The amplified signals obtained from the plurality of multichannel amplifiers 908 are then transmitted to an image segmentation device 910 for fragmenting the received image patterns to identify micro level details such as micro facial expressions and the like. These federated image patterns are then transmitted to a microcontroller 912 for further processing and verification of the identity of the user. The identity information is received in the form of a digital signal containing the received image patterns. The image acquisition device 904 is adapted to receive the digital signal and generate/transmit the digital signal to the microcontroller 912 for image recognition based on pre-stored image patterns (including such as micro facial expressions). The image recognition device 706 is adapted to sample an analog signal to generate the digital audio signal and interface with the microcontroller 912. The microcontroller 912, in association with necessary recognition software 914, is adapted to discriminate between multiple image patterns and also compare the image pattern of the user with the pre-stored image patterns to output a stream signal. The stream signal is indicative of verification of the identity information as obtained in the form of the image pattern. If the identity is verified, the user and the associated computing device may be authorized for further transactions as discussed above.

In some embodiments, various sensor modalities 708 may be contained as part of the verification components 702. These sensor modalities 708 may be coupled to the identity authorization device 712 for authorizing the access to the user and the associated computing device by the identity authorization device 712. In this embodiment, identification and authorization of the identity of the user and the associated computing device may be established based on sensed contextual patterns of the respective user and the associated computing device by external sensors such as but not limited to a GPS-based device 710. The GPS-based device 710 receives signals containing location details for verifying identity of the user based on its location. Other sensors may include such as weather sensors, location sensors, and the like. The sensor modalities 708 allow verifying the sensed contextual patterns against pre-stored patterns associated with user and the associated computing devices.

The identity authorization device 712, the processing circuit 108, the cloud gateway agent server 102, the electronic transactional system 116 and the various verification components 702 may be coupled to the blockchain device 604. The blockchain device 604 may store image-based inputs 716 received from the image recognition device 706 and/or the identity authorization device 712, voice-based inputs 718 received from the audio recognition device 704 and/or the identity authorization device 712, sensed inputs 720 received from the sensor modalities 708 and/or the identity authorization device 712, location coordinates 722 received from such as the GPS-based device 710 contained within the sensor modalities 708, and the like.

FIG. 10, with reference to FIGS. 1 through 9, illustrates an architecture 1000 for enabling an authentication, access, and verification mechanism to access and verify digital records (UGED) stored in the blockchain database 602 including such as the computer executable data files. At least some embodiments for enabling various transactions for accessing the records are discussed herein in conjunction with FIGS. 1 through 10.

In accordance with an embodiment, the entire ecosystem in which the blockchain architecture 1000 is implemented including various devices and components as shown in FIGS. 1 through 10 such as the cloud gateway agent server 102, blockchain database 604, electronic transactional system 116, verification components 702 including the identity authorization device 712, image recognition device 706, audio recognition device 704, sensor modalities 708, computing machines 104, computing stations 112, etc may be blockchain configured. The blockchain configuration may for example provide a private view referred to as private data store 1004 so that each user and/or the associated computing device such as 1002 can privately access and allow others to access certain records as appropriate and authorized based on various policies. Each user may access their records (UGED) contained within one or more computer executable data files through the dedicated private store 1004 available through a plurality of distributed access points 1006 which may be enabled in the form of distributed blocks as shown in FIG. 10, with each block providing a facility to access the computer executable data files at least in part based on access permissions and identity verification by multiple computing devices similar to 1002 associated with the users or owners of the UGED at least in part at the same time based on defined and granted access rights through a blockchain configured access scheme.

The private data store 1004 may provide a virtual storage to facilitate interaction, information exchange, and presentation of the computer executable files according to granted access for the user and the associated computing device 1002. For example, while the blockchain database 604 may store entire UGED in a distributed manner, the private data store 1004 allows a virtual storage of only limited records out of the entire records in accordance with permissions granted to the user. The virtual view of the records in the private data store 1004 may behave like a distributed relational database referencing to the blockchain database 604. The private data store 1004 may be configured to auto-hash interactions at any required interval. This compartmentalization of the records ensures that the records are secured and private as per access rights authorized to the users. The data presented on the private data store 1004 of the blockchain serves as a secure way to ensure that the private data store 1004 is in sync with any permissioned user's records (or computer executable data files) stored in the blockchain database 604.

In accordance with an embodiment, the computing devices similar to the computing device 1002 and the associated users can access the computer executable data files based on authorization and access rights granted by the identity authorization device 712 and/or the processing circuit 108 which may dynamically be updated. The blockchain configured identity authorization device 712 may be configured to validate identity of the user and the associated computing device 1002 accessing the computer executable data files for verifying ownership of the unverified computer executable data files and the partially verified computer executable data files to establish ownership. The blockchain configured identity authorization device 712 may utilize a variety of identity validation algorithms and schemes such as but not limited to facial expressions, geographical coordinates, geo-tags, gestures, muscle activity, and the like in addition to those already discussed above without limitations. In accordance with a specific type of validation scheme utilized by the blockchain identity authorization device 712, a validation scheme-based device may be utilized.

In addition to the devices shown in FIG. 10, the blockchain configured architecture 1000 may contain additional components so as to allow integrity of the computer executable data files, ownership details, verification details, user identity, and submission of comments and verification-related inputs by such as the user and the associated computing device 1002 and other users and their associated computing devices similar to the computing device 1002. This may facilitate association of an identity and associate ownership to the UGED based on the inputs thus submitted and also defining and storing a geographical and temporal identity such as when and in which location presence of the users and their respective devices such as the computing device 1002 are noted. The blockchain configured architecture 1000 may provide a crowdsourced integrity network for storing the UGED instead of locally stored information by different participants that may be tempered.

The architecture 1000 may be blockchain configured involving various blockchain devices. A network that facilitates interaction across all components may be a blockchain integrity network. The blockchain network may build trust among the various participants including the users such and associated computing terminals or devices even if the devices/terminals etc may not know one another may trust one another. The blockchain network may allow connections, transactions and access to the computer executable data files in a trusted mode. A record of transactions including access and sharing of the computer executable data files across various terminals/devices stored on the blockchain in the form of computer executable distributed ledgers 1008 may provide proof to command the necessary trust among the terminals/devices (such as those associated with various participants) to cooperate through a peer-to-peer or peer-to-client distributed digital ledger technology. The architecture 1000 may include a distributed trusted ledgers system 1010 containing the distributed blockchain ledgers 1008 associated with a plurality of computing terminals and devices such that each ledger stores a copy of the computer executable data files containing the UGED at least in part and identity information and trust notes for defining security and trust among the computing terminals and devices across the network so that each such computing terminal trusts the other computing terminal through the blockchain. The distributed ledgers system 1010 enables coding of rules-based contracts that execute when specified conditions are met. The distributed ledgers 1008 make it easier to create cost-efficient networks where any device or any information associated with a transaction (including access) may be tracked, without requiring a central point of control.

The various computing terminals or devices in the blockchain network serve as distributed peer-to-peer nodes and connections. The identity authorization device 712 may serve as a client device configured to perform the task of validating and verifying the user and the associated computing device 1002 based on the rules as defined. Each terminal/device/node in the architecture 1000, etc. may get a copy of the blockchain which may get downloaded automatically upon joining the blockchain integrity network. Every node or the device in the network is an administrator of the blockchain, and may join the network voluntarily so that the network is decentralized.

The blockchain may eliminate the risks that come with data being held centrally by storing data across the network which may include the computer executable data files containing the UGED at least in part and the identity and verification information. The blockchain security use encryption technology and validation mechanisms for security and integrity verification. The security may be enabled through public and private keys. A public key may define a user's address on the blockchain. The private key may give its owner an access to various digital assets in the network.

The embodiments herein may implement an improved form of blockchain technology to manage verification of the computer executable data files associated with the user based on consent information from the user. The user consent information and associated records of transactions and their associated consents may be maintained in a tamper-proof and immutable blockchain data structure. The blockchain data structure operates to enable the exchange of data among various parties once consent has been granted by the user through the blockchain.

Secure distributed ledgers system or trusted ledgers system 1010 of the blockchain allows identical and tamper-proof copies of the ledger 1008 (containing the computer executable files) to be maintained such that a number of independent parties provide a higher level of trust than single 'trusted third-party' solutions assuring the users and other entities in the architecture ecosystem 1000 that they will receive and can act on valid, secure, fully trusted information. Through the blockchain or the ledger-based mechanism of the embodiments, a persistent immutable store of the transactions may be provided.

In some embodiments, the cloud gateway agent server 102 may be connected to a RFID scanner 628 and a biometric scanner 630 among other data aggregating devices or equipment or mechanisms over via an I/O interface and/or over a network to aggregate the UGED. In some embodiments, the UGED may be pushed by the associated user device instead of being pulled by devices such as the RFID scanner 628 and the biometric sensor 630.

The RFID scanner 628 and the biometric scanner 630 may transmit information/data retrieved from the computing machines 104 to the cloud gateway agent server 102 or the blockchain database 602. For example, the RFID scanner 628 may scan a wearable device worn by a person who is unconscious or incapacitated at a scene of an emergency, and transmit the scanned data retrieved from the wearable device to the cloud gateway agent server 102 or the blockchain database 602.

In some embodiments, the biometric scanner 630 may scan a bodily feature of a person (or user) who is unconscious or incapacitated at a scene of an emergency, and transmit the scanned biometric data retrieved from the person to the blockchain database 602 via data bus lines.

In an example, the embodiments herein can provide a computer program product configured to include a pre-configured set of instructions, which when performed, can result in actions as stated in conjunction with the method of FIG. 2. In an example, the pre-configured set of instructions can be stored on a tangible non-transitory computer readable medium. In an example, the tangible non-transitory computer readable medium can be configured to include the set of instructions, which when performed by a device, can cause the device to perform acts similar to the ones described here.

Embodiments herein may also include tangible and/or non-transitory computer-readable storage media for carrying or having computer executable instructions or data structures stored thereon. Such non-transitory computer readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose computer or special purpose processing device to perform a certain function or group of functions. Computer-executable instructions also include program modules that are executed by computers in stand-alone or network 104 environments. Generally, program modules include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network. If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 11:
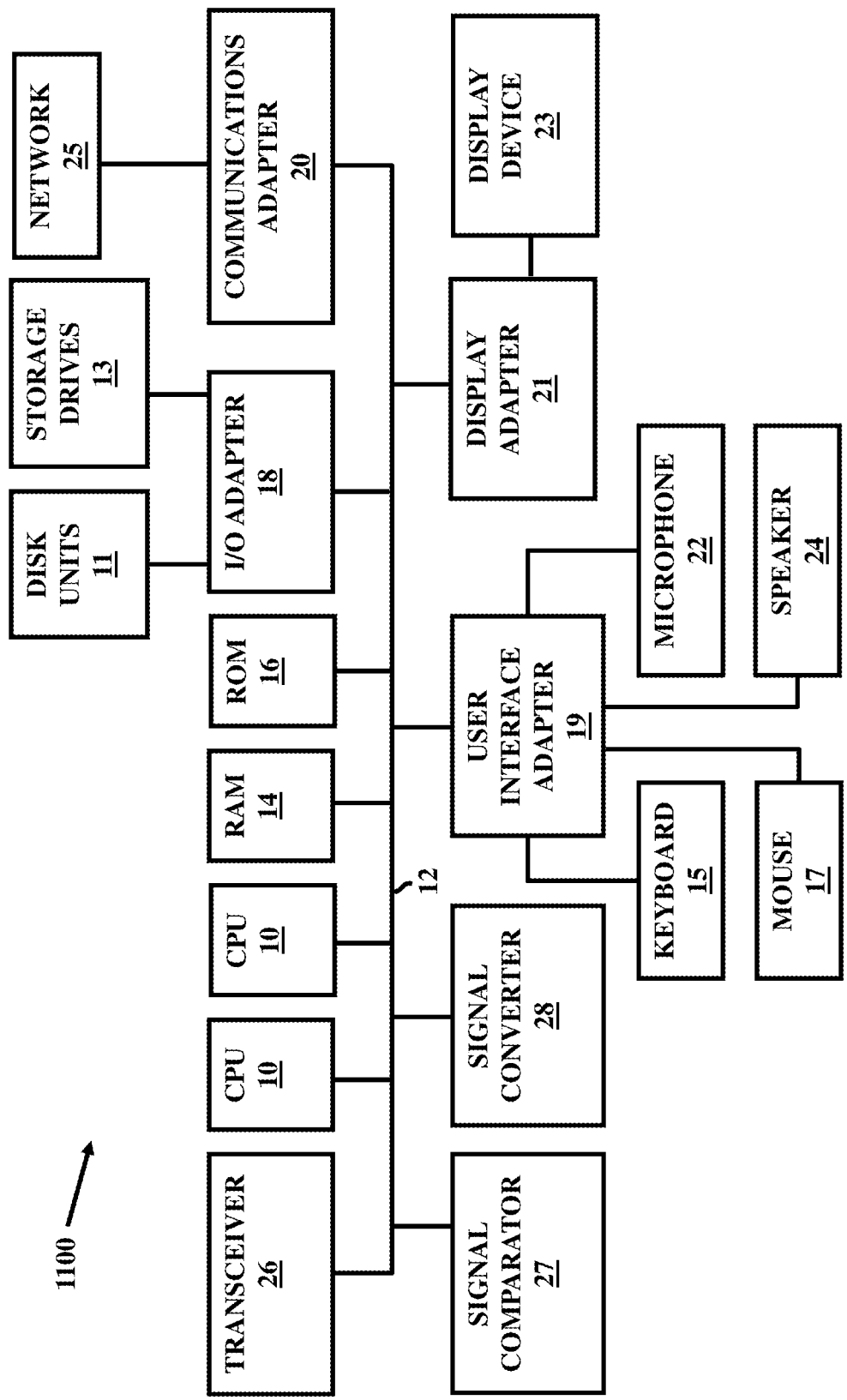
FIG. 11 illustrates generally, but not by the way of limitation, a computer system that may be used in accordance with the embodiments herein.

A representative hardware environment for practicing the embodiments herein is depicted in FIG. 11, with reference to FIGS. 1 through 10. This schematic drawing illustrates a hardware configuration of an information handling/computer system 1100 in accordance with the embodiments herein. The system 1100 comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system 1100 can read the inventive instructions on the program storage devices and follow these instructions to execute the methodology of the embodiments herein. The system 1100 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network, and a display adapter 21 connects the bus 12 to a display device 23 which may be embodied as an output device such as a monitor, printer, or transmitter, for example. Further, a transceiver 26, a signal comparator 27, and a signal converter 28 may be connected with the bus 12 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A blockchain-enabled system comprising:
a plurality of wearable devices;
a cloud gateway agent server that receives and aggregates user generated electronic data associated with a user and acquired without user intervention from one of said plurality of wearable devices located separately, wherein said user generated electronic data comprises a plurality of computer executable data files residing in said plurality of wearable devices;

an electronic record repository database communicatively coupled with said cloud gateway agent server and stores said plurality of computer executable data files and metadata associated with said plurality of computer executable data files;

a processing circuit that:
   performs natural language processing and metadata analysis of said plurality of computer executable data files to identify user verified computer executable data files and user unverified computer executable data files from among said plurality of computer executable data files;
   generates a computer data object including a plurality of query statements and approval options corresponding to each of said unverified computer executable data files;
   transmits said computer data object to an external computing machine at said user along with said unverified computer executable data files outputted on a remotely located display unit connected operatively with said external computing machine through an automatically generated notification by said processing circuit, wherein said computer data object represents an integrated view of said user generated electronic data residing on said plurality of wearable devices; and
   updates said unverified computer executable data files as new verified computer executable data files in said electronic record repository database based on an input received from said external computing machine signifying verification of said unverified computer executable data files by said user;

a rules engine communicatively coupled with said processing circuit and that executes a set of programmable rules including dictionary references, and user verification references to govern user approval, said metadata analysis and said natural language processing, wherein said rules engine determines said verification of said user verified computer executable data files by applying rules regarding user approval for different types of electronic data;

a blockchain-based identity authorization device connected communicatively to said rules engine to verify an identity of said user in association with said set of programmable rules before granting access rights to said user for verification of said unverified computer executable data files, wherein said blockchain-based device comprises one or more of an audio recognition device, an image recognition device, and sensor modalities including a global positioning system;

an electronic transactional system communicatively coupled with said electronic record repository database and said processing circuit through said cloud gateway agent server and retrieves and stores said user verified computer executable data files and said new verified computer executable data files from said electronic records repository database, and communicates electronic data messages among a plurality of computer stations located at users, service providers, and third entities, wherein said electronic data messages are obtained from said user verified computer executable data files and said new verified computer executable data files, and wherein said electronic transactional system further comprises a social networking application that dynamically changes social networking connections by interacting with said electronic transactional system and by accessing said verified computer executable data files; and a communications transmitter coupled with said electronic transactional system that transmits said electronic data messages to said plurality of computer stations identified by a user approval, wherein said computer data object comprises embedded digital text-based information of said user generated electronic data that is displayed on said display unit by launching a gateway software application, wherein said processing circuit homogenizes said user generated electronic data in a defined standard compliant format by executing computer executable data files containing said user generated electronic data, wherein said processing circuit automatically associates a numerical trust score with each of said new verified computer executable data files by using said user input signifying said verification, and wherein said processing circuit determines verification patterns by using a machine learning algorithm, and automatically classifies said computer executable data files into said user unverified computer executable data files and said user verified computer executable data files by using said verification patterns.

2. The system of claim 1, wherein at least a portion of said user generated electronic data contained in at least one of said plurality of computer executable data files is obtained by said cloud gateway agent server from a computing machine other than at said user.

3. The system of claim 2, wherein said at least a portion of said user generated electronic data is obtained from said computing machine at a service provider of said user.

4. The system of claim 1, wherein each of said plurality of wearable devices are operatively coupled with an extensible agent appliance that launches a said gateway application configured to pair said plurality of wearable devices with said cloud agent server to allow access of said plurality of computer executable data files residing on said plurality of wearable devices by said cloud agent server.

5. The system of claim 4, wherein said cloud agent server installs said gateway application remotely on said plurality of wearable devices through said extensible agent appliance.

6. The system of claim 5, wherein said gateway application is launched at said external computing machine associated with said user to allow said user to view sources of said unverified computer executable data files and to verify said unverified computer executable data files through a single-clickable user executable response against one of said approval options.

7. The system of claim 1, wherein said electronic transactional system comprises a filter circuit such that said filter circuit rejects said plurality of computer executable data files from being pushed into said electronic transactional system if said trust score associated with said plurality of computer executable data files is below a threshold limit.

8. The system of claim 1, wherein said processing circuit performs natural language processing on an embedded user natural language text note contained digitally in said plurality of computer executable data files.

9. A blockchain-enabled system comprising:
   a plurality of devices including at least one wearable device associated with a user;
   a cloud gateway agent server that receives and aggregates user generated electronic data associated with said user and acquired without user intervention from one of said plurality of devices located separately, wherein said user generated electronic data comprises a plurality of computer executable data files residing in said plurality of wearable devices;

a blockchain database communicatively coupled with said cloud gateway agent server and stores said plurality of computer executable data files and metadata associated with said plurality of computer executable data files;

a processing circuit that:
identifies user verified computer executable data files and user unverified computer executable data files from among said plurality of computer executable data files;
generates a computer data object including a plurality of query statements and approval options corresponding to each of said unverified computer executable data files;
transmits said computer data object to an external computing device at said user along with said unverified computer executable data files outputted on a remotely located display unit connected operatively with said external computing device through an automatically generated notification by said processing circuit, wherein said computer data object represents an integrated view of said user generated electronic data residing on said plurality of devices associated with said user; and
updates said unverified computer executable data files as new verified computer executable data files in said blockchain database based on an input received from said external computing device signifying verification of said unverified computer executable data files by said user;

a blockchain-based identity authorization device to verify identity of said user before granting access rights to said user for verification of said unverified computer executable data files, wherein said blockchain-based device comprises one or more of:

an audio recognition device that generates identity information in the form of a digital audio signal for voice recognition based on pre-stored voice patterns;

an image recognition device that includes an image acquisition device to receive signals containing image patterns and facial expressions for verifying identity based on image patterns;

a global positioning system-based device that receives signals containing location details for verifying identity of said user based on location;

an electronic transactional system communicatively coupled with said blockchain database and said processing circuit through said cloud gateway agent server, said electronic transactional system retrieves and stores said user verified computer executable data files and said new verified computer executable data files from said blockchain database and communicates electronic data messages to a plurality of computer stations located at different locations, wherein said electronic data messages are obtained from said user verified computer executable data files and said new verified computer executable data files; and a communications transmitter coupled with said electronic transactional system that transmits said electronic data messages to said plurality of computer stations identified by a user approval.

10. The system of claim 9, wherein said audio recognition device comprising a sound card adapted to receive identity information of said user in the form of a digital audio signal.

11. The system of claim 9, wherein said image acquisition device of said image recognition device comprising a camera for taking still or streaming images.

12. The system of claim 11, wherein said image recognition device further comprising a plurality of multichannel amplifiers such that each amplifier of said multichannel amplifiers is defined to receive a specific type of sensed information from said camera sourcing signals for said image recognition device.

13. The system of claim 9, wherein said image recognition device comprises a microcontroller, wherein said image acquisition device is adapted to receive a digital signal and transmit said digital audio signal to said microcontroller for image recognition based on pre-stored image patterns.

14. The system of claim 9, wherein at least a portion of said user generated electronic data contained in at least one of said plurality of computer executable data files is obtained by said cloud gateway agent server from a computing machine other than at said user.

15. The system of claim 9, wherein each of said plurality of devices are operatively coupled with an extensible agent appliance that launches a said gateway application configured to pair said plurality of devices with said cloud agent server to allow access of said plurality of computer executable data files residing on said plurality of devices by said cloud agent server.

16. The system of claim 15, wherein said cloud agent server installs said gateway application remotely on said plurality of devices through said extensible agent appliance.

17. The system of claim 9, further comprising a blockchain device comprising:
a specific blockchain-enabled server device;
a smart device running a custom dedicated software application, wherein said smart device is configured to engage in communication with said blockchain-enabled server device,
wherein, said blockchain device generates a smart contract configured to automatically validate a transaction using a special key over a plurality of computer executable distributed blockchain ledgers such that each of said plurality of computer executable distributed blockchain ledgers contain a copy of said computer executable data files; and
a distributed trusted ledgers system that stores said distributed blockchain ledgers over a blockchain integrity network for secured and controlled access by said user through a private key.

18. The system of claim 9, wherein said processing circuit prevents voice inputs from being received by the audio recognition device upon a predetermined number of unsuccessful voice inputs being entered into the audio recognition device and not authorized or identified by the processing circuit.

19. The system of claim 9, wherein said processing circuit prevents visual inputs from being received by the image recognition device upon a predetermined number of unsuccessful visual inputs being entered into the image recognition device and not authorized or identified by the processing circuit.

20. The system of claim 9, wherein said processing circuit transmits a user-access denial output signal upon not authenticating an identify of a user.

* * * * *